United States Patent
Rappaport et al.

(10) Patent No.: US 10,561,336 B2
(45) Date of Patent: Feb. 18, 2020

(54) METHOD AND SYSTEM FOR MONITORING THORACIC TISSUE FLUID

(75) Inventors: Dan Rappaport, Tel-Aviv (IL); Nadav Mizrahi, Tel-Aviv (IL); Shlomi Bergida, Tel-Aviv (IL); Amir Saroka, Tel-Aviv (IL); Amir Ronen, Hod-HaSharon (IL); Ilan Kochba, Modiln (IL)

(73) Assignee: Sensible Medical Innovations Ltd., Netanya (IL)

(*) Notice: Subject to any disclaimer, the term of this patent is extended or adjusted under 35 U.S.C. 154(b) by 295 days.

(21) Appl. No.: 12/676,381

(22) PCT Filed: Sep. 4, 2008

(86) PCT No.: PCT/IL2008/001199
§ 371 (c)(1),
(2), (4) Date: May 6, 2010

(87) PCT Pub. No.: WO2009/031150
PCT Pub. Date: Mar. 12, 2009

(65) Prior Publication Data
US 2010/0256462 A1    Oct. 7, 2010

Related U.S. Application Data

(60) Provisional application No. 60/969,966, filed on Sep. 5, 2007, provisional application No. 60/969,965, filed
(Continued)

(51) Int. Cl.
*A61B 5/05* (2006.01)

(52) U.S. Cl.
CPC .................................. *A61B 5/05* (2013.01)

(58) Field of Classification Search
USPC ......................................... 600/407, 409, 410
See application file for complete search history.

(56) References Cited

U.S. PATENT DOCUMENTS

| 3,534,727 A | 10/1970 | Roman |
| 4,016,868 A | 4/1977 | Allison |
| (Continued) | | |

FOREIGN PATENT DOCUMENTS

| CA | 2898342 | 7/2014 |
| EP | 0694282 | 1/1996 |
| (Continued) | | |

OTHER PUBLICATIONS

International Preliminary Report on Patentability dated Mar. 18, 2010 From the International Bureau of WIPO Re.: Application No. PCT/IL2008/001198.
(Continued)

*Primary Examiner* — Joel F Brutus

(57) ABSTRACT

A method for monitoring thoracic tissue. The method comprises intercepting reflections of electromagnetic (EM) radiation reflected from thoracic tissue of a patient in radiation sessions during a period of at least 24 hours, detecting a change of a dielectric coefficient of the thoracic tissue by analyzing respective the reflections, and outputting a notification indicating the change. The reflections are changed as an outcome of thoracic movements which occur during the period.

39 Claims, 13 Drawing Sheets
(2 of 13 Drawing Sheet(s) Filed in Color)

Related U.S. Application Data on Sep. 5, 2007, provisional application No. 60/969,963, filed on Sep. 5, 2007.

(56) References Cited

U.S. PATENT DOCUMENTS

| | | | |
|---|---|---|---|
| 4,240,445 A * | 12/1980 | Iskander et al. | 607/156 |
| 4,279,257 A | 7/1981 | Hochstein | |
| 4,381,510 A | 4/1983 | Wren | |
| 4,488,559 A | 12/1984 | Iskander | |
| 4,572,197 A | 2/1986 | Moore et al. | |
| 4,580,572 A | 4/1986 | Granek et al. | |
| 4,647,281 A | 3/1987 | Carr | |
| 4,676,252 A | 6/1987 | Trautman et al. | |
| 4,690,149 A | 9/1987 | Ko | |
| 4,877,034 A | 10/1989 | Atkins et al. | |
| 4,920,969 A | 5/1990 | Suzuki et al. | |
| 4,926,868 A | 5/1990 | Larsen | |
| 4,958,638 A | 9/1990 | Sharpe et al. | |
| 4,991,585 A * | 2/1991 | Mawhinney | 600/430 |
| 5,002,060 A * | 3/1991 | Nedivi | 600/484 |
| 5,078,134 A | 1/1992 | Heilman et al. | |
| 5,132,623 A | 7/1992 | De et al. | |
| 5,282,840 A | 2/1994 | Hudrlik | |
| 5,334,141 A | 8/1994 | Carr et al. | |
| 5,363,050 A | 11/1994 | Guo et al. | |
| 5,394,882 A | 3/1995 | Mawhinney | |
| 5,479,120 A | 12/1995 | McEwan | |
| 5,517,198 A | 5/1996 | McEwan | |
| 5,523,760 A | 6/1996 | McEwan | |
| 5,563,605 A | 10/1996 | McEwan | |
| 5,573,012 A | 11/1996 | McEwan | |
| 5,576,627 A | 11/1996 | McEwan | |
| 5,604,531 A | 2/1997 | Iddan et al. | |
| 5,728,143 A | 3/1998 | Gough et al. | |
| 5,738,102 A | 4/1998 | Lemelson | |
| 5,749,369 A | 5/1998 | Rabinovich et al. | |
| 5,766,208 A | 6/1998 | McEwan | |
| 5,804,921 A | 9/1998 | McEwan et al. | |
| 5,805,110 A | 9/1998 | McEwan | |
| 5,807,257 A | 9/1998 | Bridges | |
| 5,829,437 A | 11/1998 | Bridges | |
| 5,833,711 A | 11/1998 | Schneider, Sr. | |
| 5,861,019 A | 1/1999 | Sun et al. | |
| 5,876,353 A | 3/1999 | Riff | |
| 5,883,591 A | 3/1999 | McEwan | |
| 5,947,910 A | 9/1999 | Zimmet | |
| 5,957,861 A | 9/1999 | Combs et al. | |
| 5,964,703 A | 10/1999 | Goodman et al. | |
| 5,995,863 A | 11/1999 | Farace et al. | |
| 6,015,386 A | 1/2000 | Kensey et al. | |
| 6,026,173 A | 2/2000 | Svenson et al. | |
| 6,061,589 A * | 5/2000 | Bridges et al. | 600/430 |
| 6,064,903 A | 5/2000 | Riechers et al. | |
| 6,111,415 A | 8/2000 | Moshe | |
| 6,169,925 B1 | 1/2001 | Villaseca et al. | |
| 6,211,663 B1 | 4/2001 | Moulthrop et al. | |
| 6,233,479 B1 | 5/2001 | Haddad et al. | |
| 6,236,889 B1 | 5/2001 | Soykan et al. | |
| 6,281,843 B1 | 8/2001 | Evtioushkine et al. | |
| 6,330,479 B1 | 12/2001 | Stauffer | |
| 6,332,087 B1 | 12/2001 | Svenson et al. | |
| 6,332,091 B1 | 12/2001 | Burns et al. | |
| 6,351,246 B1 | 2/2002 | McCorkle | |
| 6,417,797 B1 | 7/2002 | Cousins et al. | |
| 6,425,878 B1 | 7/2002 | Shekalim | |
| 6,459,931 B1 | 10/2002 | Hirschman | |
| 6,484,047 B1 | 11/2002 | Vilsmeier | |
| 6,487,428 B1 | 11/2002 | Culver et al. | |
| 6,488,677 B1 | 12/2002 | Bowman et al. | |
| 6,494,829 B1 | 12/2002 | New, Jr. et al. | |
| 6,496,711 B1 | 12/2002 | Athan et al. | |
| 6,512,949 B1 | 1/2003 | Combs et al. | |
| 6,551,252 B2 | 4/2003 | Sackner et al. | |
| 6,574,510 B2 | 6/2003 | Von Arx et al. | |
| 6,577,709 B2 | 6/2003 | Tarr | |
| 6,590,545 B2 | 7/2003 | McCorkle | |
| 6,675,045 B2 | 1/2004 | Mass et al. | |
| 6,682,480 B1 | 1/2004 | Habib et al. | |
| 6,687,523 B1 | 2/2004 | Jayaramen et al. | |
| 6,746,404 B2 | 6/2004 | Schwartz | |
| 6,766,201 B2 | 7/2004 | Von Arx et al. | |
| 6,770,070 B1 | 8/2004 | Balbierz | |
| 6,783,499 B2 | 8/2004 | Schwartz | |
| 6,788,262 B1 | 9/2004 | Adams et al. | |
| 6,802,811 B1 | 10/2004 | Slepian | |
| 6,809,701 B2 | 10/2004 | Amundson et al. | |
| 6,849,046 B1 | 2/2005 | Eyal-Bickels et al. | |
| 6,909,397 B1 | 6/2005 | Greneker, III et al. | |
| 6,917,833 B2 | 7/2005 | Denker et al. | |
| 6,954,673 B2 | 10/2005 | Von Arx et al. | |
| 6,972,725 B1 | 12/2005 | Adams | |
| 7,006,856 B2 | 2/2006 | Baker, Jr. et al. | |
| 7,024,248 B2 | 4/2006 | Penner et al. | |
| 7,047,058 B1 | 5/2006 | Dvorsky et al. | |
| 7,072,718 B2 | 7/2006 | Von Arx et al. | |
| 7,077,810 B2 | 7/2006 | Lange et al. | |
| 7,110,823 B2 | 9/2006 | Whitehurst et al. | |
| 7,116,276 B2 | 10/2006 | Lee | |
| 7,122,012 B2 | 10/2006 | Bouton et al. | |
| 7,135,871 B1 | 11/2006 | Pelletier | |
| 7,229,415 B2 | 6/2007 | Schwartz | |
| 7,315,170 B2 | 1/2008 | Sakayori | |
| 7,316,658 B2 | 1/2008 | Gagne | |
| 7,330,034 B1 | 2/2008 | Pelletier et al. | |
| 7,387,610 B2 | 6/2008 | Stahmann et al. | |
| 7,445,605 B2 | 11/2008 | Overall et al. | |
| 7,450,077 B2 | 11/2008 | Waterhouse et al. | |
| 7,483,752 B2 | 1/2009 | Von Arx et al. | |
| 7,561,908 B2 | 7/2009 | Glukhovsky et al. | |
| 7,591,792 B2 | 9/2009 | Bouton | |
| 7,613,522 B2 | 11/2009 | Christman et al. | |
| 7,628,757 B1 | 12/2009 | Koh | |
| 7,674,244 B2 | 3/2010 | Kalafut et al. | |
| 7,686,762 B1 | 3/2010 | Najafi et al. | |
| 7,725,150 B2 | 5/2010 | Tupin, Jr. et al. | |
| 7,729,776 B2 | 6/2010 | Von Arx et al. | |
| 7,736,309 B2 | 6/2010 | Miller et al. | |
| 7,756,587 B2 | 7/2010 | Penner et al. | |
| 7,825,667 B2 | 11/2010 | Fang et al. | |
| 7,837,629 B2 | 11/2010 | Bardy | |
| 7,844,341 B2 | 11/2010 | Von Arx et al. | |
| 7,860,574 B2 | 12/2010 | Von Arx et al. | |
| 7,872,613 B2 | 1/2011 | Keilman et al. | |
| 8,032,199 B2 | 10/2011 | Linti et al. | |
| 8,235,949 B2 | 8/2012 | Hack et al. | |
| 2003/0036674 A1 | 2/2003 | Bouton | |
| 2003/0036713 A1 * | 2/2003 | Bouton et al. | 600/587 |
| 2003/0128808 A1 * | 7/2003 | Kindlein et al. | 378/65 |
| 2004/0006279 A1 | 1/2004 | Arad (Abboud) | |
| 2004/0073093 A1 * | 4/2004 | Hatlestad | 600/300 |
| 2004/0148021 A1 | 7/2004 | Cartledge et al. | |
| 2004/0186395 A1 | 9/2004 | Vastano | |
| 2004/0249257 A1 | 12/2004 | Tupin, Jr. et al. | |
| 2004/0249258 A1 | 12/2004 | Tupin, Jr. et al. | |
| 2004/0254457 A1 | 12/2004 | Van der Weide | |
| 2005/0065567 A1 | 3/2005 | Lee et al. | |
| 2005/0107719 A1 * | 5/2005 | Arad (Abbound) | 600/547 |
| 2005/0124908 A1 | 6/2005 | Belalcazar et al. | |
| 2005/0149139 A1 | 7/2005 | Plicchi et al. | |
| 2005/0171396 A1 | 8/2005 | Pankratov et al. | |
| 2005/0177061 A1 | 8/2005 | Alanen et al. | |
| 2006/0058606 A1 | 3/2006 | Davis et al. | |
| 2006/0235289 A1 | 10/2006 | Wesselink et al. | |
| 2006/0258952 A1 | 11/2006 | Stahmann et al. | |
| 2006/0293609 A1 | 12/2006 | Stahmann et al. | |
| 2007/0032749 A1 | 2/2007 | Overall et al. | |
| 2007/0066904 A1 | 3/2007 | Wiesmann et al. | |
| 2007/0088221 A1 | 4/2007 | Stahmann | |
| 2007/0123770 A1 | 5/2007 | Bouton et al. | |
| 2007/0163584 A1 | 7/2007 | Bohm et al. | |
| 2007/0197878 A1 | 8/2007 | Shklarski | |
| 2007/0238914 A1 * | 10/2007 | Royalty et al. | 600/16 |
| 2008/0097530 A1 | 4/2008 | Muccio et al. | |
| 2008/0103440 A1 | 5/2008 | Ferren et al. | |

(56) References Cited

U.S. PATENT DOCUMENTS

| | | |
|---|---|---|
| 2008/0200802 A1 | 8/2008 | Bhavaraju et al. |
| 2008/0200803 A1 | 8/2008 | Kwon et al. |
| 2008/0224688 A1 | 9/2008 | Rubinsky et al. |
| 2008/0269589 A1 | 10/2008 | Thijs et al. |
| 2008/0283290 A1 | 11/2008 | Niino et al. |
| 2008/0288028 A1 | 11/2008 | Larson et al. |
| 2009/0043223 A1 | 2/2009 | Zhang et al. |
| 2009/0149918 A1 | 6/2009 | Krulevitch et al. |
| 2009/0227882 A1 | 9/2009 | Foo |
| 2009/0228001 A1 | 9/2009 | Pacey |
| 2009/0228075 A1 | 9/2009 | Dion |
| 2009/0241972 A1 | 10/2009 | Keilman et al. |
| 2009/0248129 A1 | 10/2009 | Keilman et al. |
| 2010/0056907 A1 | 3/2010 | Rappaport et al. |
| 2010/0256462 A1 | 10/2010 | Rappaport et al. |
| 2011/0025295 A1 | 2/2011 | Saroka et al. |
| 2011/0319746 A1 | 12/2011 | Kochba et al. |
| 2013/0281800 A1 | 10/2013 | Saroka et al. |
| 2017/0156626 A1 | 6/2017 | Kochba et al. |

FOREIGN PATENT DOCUMENTS

| | | |
|---|---|---|
| EP | 1600892 | 11/2005 |
| JP | 2004-528864 | 9/2004 |
| JP | 2005-531386 | 10/2005 |
| JP | 2005-334298 | 12/2005 |
| JP | 2007-509353 | 4/2007 |
| WO | WO 99/39728 | 8/1999 |
| WO | WO 00/71207 | 11/2000 |
| WO | WO 02/053228 | 7/2002 |
| WO | WO 03/009753 | 2/2003 |
| WO | WO 2004/004539 | 1/2004 |
| WO | WO 2005/043100 | 5/2005 |
| WO | WO 2005/074361 | 8/2005 |
| WO | WO 2005/094369 | 10/2005 |
| WO | WO 2007/010460 | 1/2007 |
| WO | WO 2007/055491 | 5/2007 |
| WO | WO 2008/002251 | 1/2008 |
| WO | WO 2008/122056 | 10/2008 |
| WO | WO 2009/031149 | 3/2009 |
| WO | WO 2009/031150 | 3/2009 |
| WO | WO 2011/141915 | 11/2011 |

OTHER PUBLICATIONS

International Preliminary Report on Patentability dated Mar. 18, 2010 From the International Bureau of WIPO Re.: Application No. PCT/IL2008/001199.

International Search Report dated Feb. 4, 2009 From the International Searching Authority Re.: Application No. PCT/IL2008/001198.

International Search Report dated Jan. 23, 2009 From the International Searching Authority Re.: Application No. PCT/IL2008/001199.

Written Opinion dated Feb. 4, 2009 From the International Searching Authority Re.: Application No. PCT/IL2008/001198.

Written Opinion dated Jan. 23, 2009 From the International Searching Authority Re.: Application No. PCT/IL2008/001199.

Azevedo et al "Micropower Impulse Radar", Science & Technologies Review, Feb. 17-29, 1996.

Billich "Bio-Medical Sensing Using Ultra Wideband Communications and Radar Technology", PhD Proposal, Department of Information and Telecommunication Technology—University of Trento, Italy—Jan. 2006 (10 pages).

Gentili et al "A Versatile Microwave Plethysmograph for the Monitoring of Physiological Parameters", IEEE Transactions on Biomedical Engineering 49(10) 1204-1210, Oct. 2002.

Juweid et al. "Positron-Emission Tomography and Assessment of Cancer Therapy", The New England Journal of Medicine, 354(5): 496-507, Feb. 2, 2006.

Kagawa et al. "Advanced Exercise Control Using Miniature ECG and 3D Acceleration Sensors", D&D Forum on Telemedicine Systems: Issues, design, Development and Standardization at Globecom 2008, New Orleans, Louisiana, USA, 23 P., Dec. 2, 2008.

Katzeff et al. "Exercise Stress Testing and an Electromechanical S Wace of the Electrocardiogram", South African Medical Journal, 49(27): 1088-1090, Jun. 28, 1975.

Kerckhofs et al. "Homogeneity of Cardiac Contraction Despite Physiological Asynchrony of Depolarization: A Model Study", Annals of Biomedical Engineering, 31: 536-547, 2003.

Lee et al. "Noninvasive Tests in Patients With Stable Coronary Artery Disease", The New England Journal of Medicine, 344(24): 1840-1845, Jun. 14, 2001.

Park et al. "An Ultra-Wearable, Wireless, Low Power ECG Monitoring System", Proceedings of the IEEE Biomedical Circuits and Systems Conference, BioCAS 2006, London, UK, p. 241-244, Nov. 29-Dec. 1, 2006.

Pedersen et al "An Investigation of the Use of Microwave Radiation for Pulmonary Diagnostics", Communications—IEEE Transcations on Biomedical Engineering, p. 410-412, Sep. 1976.

Schiller "Noninvasive Monitoring of Tumors", The New England Journal of Medicine, 359(4): 418-420, Jul. 24, 2008.

Smiseth et al. "Regional Left Ventricular Electric and Mechanical Activation and Relaxation", JACC, Journal of the American College of Cardiology, 47(1): 173-174, Jan. 3, 2006.

Thornton "Optimization of Protocols for Computed Tomography Coronary Angiography", Supplement to Applied Radiology, p. 54-62, Jun. 2002.

Yamokoski et al "OptiVol® Fluid Status Monitoring With an Implantable Cardiac Device: A Heart Failure Managaement System. ", 4:(6) 775-780 (doi:10.1586/17434440.4.6.775), Nov. 2007.

Zito et al "Wearable System-on-a-Chip Pulse Radar Sensors for the Health Care: System Overview", 21st Conference on Advanced Information Networking and Applications Workshop (AINAW'07), University of Pisa, Italy—2007, IEEE.

Zlochiver et al "A Portable Bio-Impedance System for Monitoring Lung Resistivity", Medical Engineering & Physics, 29:(1), 93-100.

Official Action dated Apr. 4, 2012 From the US Patent and Trademark Office Re. U.S. Appl. No. 12/676,385.

Restriction Official Action dated Jun. 7, 2012 From the US Patent and Trademark Office Re. U.S. Appl. No. 12/544,314.

Hill-Rom "The Vest® Airway Clearance System. Information for Physicians", Hill-Rom, Retrieved From the Internet, 3 P., Nov. 24, 2011.

Jafari et al. "Ultrawideband Radar Imagingn System for Biomedical Applications", Journal of Vacuum Science and Technology A: Vacuum, Surfaces, and Films, 24(3): 752-757, May/Jun. 2006.

Li et al. "An Overview of Ultra-Wideband Microwave Imaging Via Space-Time Beamforming for Early-Stage Breast-Cancer Detection", IEEE Antennas and Propagation Magazine, 47(1): 19-34, Feb. 2005.

Mcancy et al. "Near-Field Microwave Imaging of Biologically-Based Materials Using a Monopole Transceiver System", IEEE Transactions on Microwave Theory and Techniques, 46(1): 31-45, Jan. 1998.

Pedersen et al "An Investigation of the Use of Microwave Radiation for Pulmonary Diagnostics", IEEE Transactions on Biomedical Engineering, 23(5): 410-412, Sep. 1976.

Shea et al. "Contrast-Enhanced Microwave Imaging of Breast Tumors: A Computational Study Using 3D Realistic Numerical Phantoms", Inverse Problems, 26: 1-22, 2010.

Zhou et al. "On the Resolution of UWB Microwave Imaging of Tumors in Random Breast Tissue", IEEE International Symposium of the Antennas and Propagation Society, Jul. 3-8, 2005, 3A: 831-834, Jul. 2005.

International Search Report and the Written Opinion dated Jun. 15, 2010 From the International Searching Authority Re.: Application No. PCT/IL2010/000182.

Semenov et al. "Three-Dimensional Microwave Tomography: Initial Experimental Imaging of Animals", IEEE Transactions on Biomedical Engineering, XP011007196, 49(1): 55-63, Jan. 2002. Abstract, p. 56, col. 1, Lines 6, 7.

International Preliminary Report on Patentability dated Sep. 15, 2011 From the International Bureau of WIPO Re. Application No. PCT/IL2010/000182.

(56) References Cited

OTHER PUBLICATIONS

Official Action dated Oct. 15, 2012 From the US Patent and Trademark Office Re. U.S. Appl. No. 12/846,861.
Communication Pursuant to Article 94(3) EPC dated May 6, 2013 From the European Patent Office Re. Application No. 10712583.3.
Advisory Action Before the Filing of an Appeal Brief dated Jun. 6, 2013 From the US Patent and Trademark Office Re. U.S. Appl. No. 12/676,385.
Applicant-Initiated Interview Summary dated Jun. 13, 2013 From the US Patent and Trademark Office Re. U.S. Appl. No. 12/676,385.
Office Action dated Jun. 5, 2013 From the Israel Patent Office Re. Application No. 214973 and its Translation into English.
Official Action dated Jul. 5, 2013 From the US Patent and Trademark Office Re. U.S. Appl. No. 12/846,861.
Supplementary European Search Report and the European Search Opinion dated Feb. 13, 2013 From the European Patent Office Re. Application No. 08789867.2.
Supplementary European Search Report and the European Search Opinion dated Feb. 14, 2013 From the European Patent Office Re. Application No. 08808013.0.
Official Action dated Dec. 19, 2012 From the US Patent and Trademark Office Re. U.S. Appl. No. 12/544,314.
Official Action dated Dec. 20, 2012 From the US Patent and Trademark Office Re. U.S. Appl. No. 12/676,385.
Communication Pursuant to Rules 70(2) and 70a(2) EPC dated Mar. 5, 2013 From the European Patent Office Re. Application No. 08808013.0.
Official Action dated Mar. 25, 2013 From the US Patent and Trademark Office Re. U.S. Appl. No. 13/254,852.
Jiang et al. "Ultrasound-Guided Microwave Imaging of Breast Cancer: Tissue Phantom and Pilot Clinical Experiments", Medical Physics, 32(8): 2528-2535, Aug. 2005.
Kramer et al. "Dielectric Measurement of Cerebral Water Content Using a Network Analyzer", Neurological Research, 14: 255-258, Jun. 1992.
Nopp et al. "Dielectric Properties of Lung Tissue as a Function of Air Content", Physics in Medicine and Biology, 38(6): 699-716, Jun. 1993.
Notice of Reason for Rejection dated Jan. 31, 2014 From the Japanese Patent Office Re. Application No. 2010-523644 and its Translation into English.
Advisory Action Before the Filing of an Appeal Brief dated Apr. 22, 2014 From the US Patent and Trademark Office Re. U.S. Appl. No. 13/254,852.
Communication Pursuant to Article 94(3) EPC dated Mar. 19, 2014 From the European Patent Office Re. Application No. 08789867.2.
Official Action dated Mar. 11, 2014 From the US Patent and Trademark Office Re. U.S. Appl. No. 12/544,314.
Applicant-Initiated Interview Summary dated May 16, 2014 From the US Patent and Trademark Office Re. U.S. Appl. No. 13/254,852.
Communication Pursuant to Article 94(3) EPC dated May 22, 2014 From the European Patent Office Re. Application No. 10712583.3.
Office Action dated Apr. 28, 2014 From the Israel Patent Office Re. Application No. 214973 and its Translation into English.
Official Action dated Oct. 11, 2013 From the US Patent and Trademark Office Re. U.S. Appl. No. 12/544,314.
Translation of Notice of Reason for Rejection dated Sep. 24, 2013 From the Japanese Patent Office Re. Application No. 2010-523644.
Applicant-Initiated Interview Summary dated Dec. 11, 2013 From the US Patent and Trademark Office Re. U.S. Appl. No. 12/544,314.
Communication Pursuant to Article 94(3) EPC dated Sep. 27, 2013 From the European Patent Office Re. Application No. 08808013.0.
Communication Pursuant to Article 94(3) EPC dated Oct. 29, 2013 From the European Patent Office Re. Application No. 08789867.2.
Official Action dated Dec. 12, 2013 From the US Patent and Trademark Office Re. U.S. Appl. No. 13/254,852.
Meaney et al. "Microwave Imaging for Neoadjuvant Chemotherapy Monitoring", First European Conference on Antennas and Propagation, EuCAP 2006, Nice, France, Nov. 6-10, 2006, p. 1-4, Nov. 2006.

Panetta "A Mathematical Model of Periodically Pulsed Chemotherapy: Tumor Recurrence and Metastasis in a Competitive Environment", Bulletin of Methematical Biology, 58(3): 425-447, 1996.
Official Action dated Nov. 3, 2014 From the US Patent and Trademark Office Re. U.S. Appl. No. 12/544,314.
Advisory Action Before the Filing of an Appeal Brief dated Mar. 18, 2015 From the US Patent and Trademark Office Re. U.S. Appl. No. 12/544,314.
Applicant-Initiated Interview Summary dated Feb. 20, 2015 From the US Patent and Trademark Office Re. U.S. Appl. No. 13/254,852.
Communication Pursuant to Article 94(3) EPC dated Aug. 4, 2014 From the European Patent Office Re. Application No. 08808013.0.
Official Action dated Sep. 4, 2014 From the US Patent and Trademark Office Re. U.S. Appl. No. 13/254,852.
Restriction Official Action dated Jul. 2, 2015 From the US Patent and Trademark Office Re. U.S. Appl. No. 13/922,299.
Official Action dated Jun. 10, 2015 From the US Patent and Trademark Office Re. U.S. Appl. No. 13/254,852.
Fear et al. "Microwaves for Breast Cancer Detection", IEEE Potentials, 22(1): 12-18, Feb. 25, 2003.
Advisory Action Before the Filing of an Appeal Brief dated Oct. 21, 2015 From the US Patent and Trademark Office Re. U.S. Appl. No. 13/254,852.
Notice of Reason for Rejection dated Oct. 23, 2015 From the Japanese Patent Office Re. Application No. 2015-000023 and its Translation into English.
Official Action dated Oct. 2, 2015 From the US Patent and Trademark Office Re. U.S. Appl. No. 13/922,299.
Official Action dated Sep. 25, 2015 From the US Patent and Trademark Office Re. U.S. Appl. No. 12/544,314.
Communication Pursuant to Article 94(3) EPC dated Feb. 19, 2016 From the European Patent Office Re. Application No. 08789867.2.
Office Action dated Dec. 14, 2015 From the Israel Patent Office Re. Application No. 239240 and its Translation into English.
Communication Pursuant to Article 94(3) EPC dated Apr. 16, 2015 From the European Patent Office Re. Application No. 10712583.3.
Communication Pursuant to Article 94(3) EPC dated Apr. 29, 2015 From the European Patent Office Re. Application No. 08789867.2.
Official Action dated Mar. 14, 2016 From the US Patent and Trademark Office Re. U.S. Appl. No. 13/254,852.
Summons to Attend Oral Proceedings Pursuant to Rule 115(1) EPC dated Mar. 16, 2016 From the European Patent Office Re. Application No. 10712583.3.
Fear et al. "Enhancing Breast Tumor Detection With Near-Field Imaging", IEEE Microwave Magazine, pp. 48-56, Mar. 2002.
Winters et al. "Estimation of the Frequency-Dependent Average Dielectric Properties of Breast Tissue Using a Time-Domain Inverse Scattering Technique" IEEE Transactions on Antennas and Propagation, 54(11): 3517-3528, Nov. 2006.
Winters et al. "Three-Dimensional Microwave Breast Imaging: Dispersive Dielectric Properties Estimation Using Patient-Specific Basis Functions", IEEE Transactions on Medical Imaging, 28(7): 969-981, Jul. 2007.
Translation of Reason for Rejection dated Jul. 29, 2016 From the Japanese Patent Office Re. Application No. 2015-000023.
Official Action dated May 25, 2016 From the US Patent and Trademark Office Re. U.S. Appl. No. 13/922,299.
Gabriel "Compilation of the Dielectric Properties of Body Tissues at RF and Microwave Frequencies", Final Technical Report for the Period Sep. 15, 1993 to Dec. 14, 1994, p. 1-21, Jan. 1996.
Schantz "Introduction to Ultra-Wideband Antennas", IEEE Conference, On Ultra Wideband Systems and Technologies, in Brownsboro, AL, USA, on Nov. 16-19, 2003, p. 1-9, 2003.
Official Action dated Mar. 9, 2017 From the US Patent and Trademark Office Re. U.S. Appl. No. 13/922,299. (40 pages).
Summons to Attend Oral Proceedings Pursuant to Rule 115(1) EPC dated Dec. 23, 2016 From the European Patent Office Re. Application No. 08789867.2. (4 Pages).
European Search Report and the European Search Opinion dated Apr. 3, 2017 From the European Patent Office Re. Application No. 17153865.5. (7 Pages).
Interview Summary dated Jun. 8, 2017 From the US Patent and Trademark Office Re. U.S. Appl. No. 13/922,299. (3 pages).

(56) References Cited

OTHER PUBLICATIONS

Official Action dated Apr. 7, 2017 From the US Patent and Trademark Office Re. U.S. Appl. No. 154/436,902. (41 Pages).
Official Action dated May 25, 2017 From the US Patent and Trademark Office Re. U.S. Appl. No. 12/544,314. (33 pages).
Iskander et al. A Microwave Method for Measuring Changes in Lung Water Content: Numerical Simulation, IEEE Transactions on Biomedical Engineering 28(12): 797-804, Dec. 1981.
Pierard et al. "Stress Testing in Valve Desease", Heart 93:766-772, 2007.
Official Action dated Jun. 29, 2018 From the US Patent and Trademark Office Re. U.S. Appl. No. 13/922,299. (27 pages).
McClelland et al. "A Continuous 40 Motion Model from Multiple Respiratory Cycles for Use in Lung Radiotherapy", Medical Physics, 33(9): 3348-3358, Sep. 2006.
Communication Pursuant to Article 94(3) EPC dated May 18, 2018 From the European Patent Office Re. Application No. 17153865.5. (4 Pages).
Official Action dated Jun. 4, 2018 From the US Patent and Trademark Office Re. U.S. Appl. No. 15/436,902. (44 pages).
Official Action dated Nov. 16, 2017 From the US Patent and Trademark Office Re. U.S. Appl. No. 15/436,902. (45 pages).
Wikipedia "Electronic Packaging", Retrieved from wikipedia.org, 4 Pages, Published Online on Dec. 2006.
Official Action dated Apr. 4, 2018 From the US Patent and Trademark Office Re. U.S. Appl. No. 12/544,314. (22 pages).
European Search Report and the European Search Opinion dated Sep. 20, 2018 From the European Patent Office Re. Application No. 17020594.2. (7 Pages).
Official Action dated Apr. 16, 2019 From the US Patent and Trademark Office Re. U.S. Appl. No. 15/436,902. (27 pages).
Communication Pursuant to Article 94(3) EPC dated Dec. 17, 2018 From the European Patent Office Re. Application No. 17153865.5. (6 Pages).
Semenov et al. "Dielectrical Spectroscopy of Canine Myocardium During Acute Ischemia and Hypoxia at Frequency Spectrum From 100 kHz to 6 GHz", IEEE Transactions on Medical Imaging, XP011076314, 21(6): 703-707, Jun. 2002.
Official Action dated Jul. 13, 2016 From the US Patent and Trademark Office Re. U.S. Appl. No. 12/544,314.

\* cited by examiner

METHOD AND SYSTEM FOR MONITORING THORACIC TISSUE FLUID

RELATED APPLICATIONS

This application is a National Phase of PCT Patent Application No. PCT/IL2008/001199 having International filing date of Sep. 4, 2008, which claims the benefit of U.S. Provisional Patent Application Nos. 60/969,966, 60/969,965 and 60/969,963, all of which were filed on Sep. 5, 2007.

PCT Patent Application No. PCT/IL2008/001199 was also co-filed with PCT Patent Application No. PCT/IL2008/001198 on Sep. 4, 2008.

The contents of the above applications are all incorporated herein by reference.

FIELD AND BACKGROUND OF THE INVENTION

The present invention, in some embodiments thereof, relates to a system and a method for monitoring pathological condition of a patient and, more particularly, but not exclusively, to a system and a method for monitoring pathological and physiological condition of a user using EM radiation.

Commonly known, pulmonary edema, the build-up of interstitial fluids and alveolar fluids in the spaces outside the blood vessels of the lungs, is a common complication of heart disorders, for example heart failure that raises the intravascular blood pressure followed by the removal of fluids from the lungs vascular circulation or a direct injury to the lungs parenchyma. The build-up of interstitial fluid and alveolar fluids is usually quantified as extra vascular lung water (EVLW), a volume parameter that identifies fluid overload. In a healthy lung, the fluid content is approximately 80% of the lung weight and includes intravascular and extravascular fluids. The normal values of the intravascular fluid volume of a healthy lung are approximately 500 cubic centimeters (cc). The normal values of the extracellular fluid volume of a healthy lung are approximately between 200 cc and 470 cc of loose interlobular fluid and alveolar interstitial fluids. Typically, symptoms of lung edema appear when the lung of the patient contains between 500 cc and 700 cc more than the normal values. Pulmonary edema can be a chronic condition, or it can develop suddenly and quickly become life threatening. The life-threatening type of pulmonary edema occurs when a large amount of fluid suddenly shifts from the pulmonary blood vessels into the extravascular area of the lungs.

Known etiologies of pulmonary edema include the following:
1. Pulmonary edema secondary to altered capillary permeability-includes acute respiratory deficiency syndrome (ARDS), trauma, infectious causes, inhaled toxins, circulating exogenous toxins, vasoactive substances, disseminated intravascular coagulopathy (DIC), immunologic processes reactions, uremia, near drowning, and other aspirations.
2. Pulmonary edema secondary to increased pulmonary capillary pressure-comprises cardiac causes and non-cardiac causes, including pulmonary venous thrombosis, stenosis or veno-occlusive disease, and volume overload.
3. Pulmonary edema secondary to decreased oncotic pressure found with hypoalbuminemia.
4. Pulmonary edema secondary to lymphatic insufficiency.
5. Pulmonary edema secondary to large negative pleural pressure with increased end expiratory volume.
6. Pulmonary edema secondary to mixed or unknown mechanisms including high altitude pulmonary edema (HAPE), neurogenic pulmonary edema, heroin or other overdoses, pulmonary embolism, eclampsia, postcardioversion, postanesthetic, postextubation, and post-cardiopulmonary bypass.

Pulmonary edema may be the first sign of heart failure exacerbation. When the heart's main chamber, the left ventricle, is weakened and does not function properly, the ventricle does not completely eject its contents, causing blood to back up and rise of left atrial pressure (LAP). The rise of LAP affects the pulmonary blood vessels that transport the blood to the left atrium by increasing the intravascular blood pressure, leading to fluid leaks into the extravascular space at first, and into the alveolar space as the phenomenon progresses.

Today, pulmonary edema is usually diagnosed when dyspnea is present and by a physical examination which confirms the presence of rales and further confirmed roughly through chest radiography. Clinical examination of chest radiography and blood gases, either alone or together, has proven to be relatively poor indicators of the amount of lungs edema or in changes in edema with treatment, of various etiologies, see Halperin B D, F. T., Mihm F G, Chiles C, Guthaner D F, Blank N E, Evaluation of the portable chest roetgenogram for quantifying extravascular lungs water in critically ill adults. Chest, 1985. 88: p. 649-652, which is incorporated herein by reference. Direct measurements of EVLWI have shown better results, see Baudendistel L, S. J., Kaminski D L, Comparison of double indicator thermodilution measurements of extravascular lungs water (EVLW) with radiographic estimation of lungs water in trauma patients. J Trauma, 1982. 22: p. 983-988, which is incorporated herein by reference.

During the years, systems and methods for monitoring pulmonary edema have been developed. For example U.S. Pat. No. 6,931,272, filed on Apr. 29, 2003 describes a medical device for monitoring fluid retention that may accompany congestive heart failure and pulmonary edema. The medical device, which may be an implanted pacemaker or an external defibrillator, senses electrical signals associated with the periodic depolarization and re-polarization of a heart. The device processes the electrical signals to obtain one or more "cardiac parameters," which reflect pulmonary edema. By monitoring the cardiac parameters, the device monitors pulmonary edema. Cardiac parameters comprise the amplitude of the QRS complex, the integral of the QRS complex, or the integral of the QRST segment and the like. When the device detects fluid buildup, the device may respond by taking remedial action and/or generating an alert.

Similarly, trans-pulmonary bio-impedance methods, measure the impedance of specific lung segments which is correlative with the congestion level of the lungs, see Zlochiver, M et. al. A portable bio-impedance system for monitoring lung resistivity, Medical Engineering & Physics, Volume 29, Issue 1, Pages 93-100 S and Laura M Yamokoskiat et al, OptiVol® fluid status monitoring with an implantable cardiac device: a heart failure management system, November 2007, Vol. 4, No. 6, Pages 775-780 (doi:10.1586/17434440.4.6.775), which are incorporated herein by reference.

Alternative means to assess the congestion level is achieved by estimating the rise of the LAP which was found to correlate with the leak of fluids to the extravascular space, see Anthony S. Fauci et. al. Harrison's, principles of internal medicine. 17th ed., McGraw-Hill Professional.

SUMMARY OF THE INVENTION

According to an aspect of some embodiments of the present invention there is provided a method for detecting a change in at least one thoracic tissue. The method comprises intercepting at least one reflection of electromagnetic (EM) radiation reflected from the at least one thoracic tissue of a patient in at least one radiation session during a period of at least 24 hours, detecting a change of a dielectric coefficient of the at least one thoracic tissue by analyzing respective the at least one reflection, and outputting a notification indicating the change. The at least one reflection is changed as an outcome of at least one thoracic movement during the period.

Optionally, thoracic tissue is a pulmonary tissue.

Optionally, at least some of the intercepting is performed while the patient being ambulatory.

Optionally, the change is indicative of thoracic tissue fluid content change in the at least one thoracic tissue.

Optionally, the analyzing comprises identifying, in a signal based on the at least one reflection, a segment representing the at least one thoracic tissue, and detecting the change according to the segment.

More optionally, the identifying comprises using a predefined chest wall model for identifying the segment.

More optionally, the method further comprises adjusting the predefined chest wall model according to medical information related to the patient before the identifying.

More optionally, the identifying comprises identifying at least one tissue transition in the signal and using the at least one tissue transition for identifying the segment.

More optionally, the detecting comprises identifying a breathing cycle of the patient, wherein the segment is identified according to the breathing cycle.

More optionally, the thoracic tissue fluid content comprises a combination of extravascular lung water (EVLW) level, intravascular lung water, and intracellular water.

Optionally, the analyzing comprises identifying a current posture of the patient and performing the detecting with respect to the effect of the current posture on the change.

Optionally, the method comprises identifying an activity level, the detecting being performed with respect to the effect of the activity level on the change.

Optionally, the at least one thoracic tissue is between the pulmonary tissue and the chest wall of the patient.

Optionally, the at least one thoracic tissue is between the pericardium and the heart of the patient.

Optionally, the method comprises identifying a match between the change and at least one value indicative of at least one of a pathologic pattern, wherein the notification is configured for indicating the at least one pathologic pattern.

More optionally, the at least one pathologic pattern is of a member selected from a group consisting of: a degenerative process, acute respiratory distress syndrome (ARDS), congestive heart failure (CHF), trauma, an atelectasis, a post-operative atelectasis, a postoperative process, an osculated bronchus, a pulmonary inflammation progress, a pulmonary blood accumulation, an infectious causes, an inhaled toxins, a circulating exogenous toxins, a vasoactive substances, a disseminated intravascular coagulopathy (DIC), a immunologic processes reactions, a uremia, a post drowning lung water level, a pulmonary venous thrombosis, a stenosis, a veno-occlusive disease, a hypoalbuminemia, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, and post-cardiopulmonary bypass.

Optionally, the method comprises monitoring a biological parameter of the patient using a medical sensor, the detecting being performed according to a combination of data based on the at least one reflection and the biological parameter.

More optionally, the medical sensor is selected from a group consisting of an electrocardiogram (ECG), an electromyogram (EMG), an ultrasound transducer, a pulse oximeter, a blood pressure sensor, coagulometer, and optical blood saturation detector.

More optionally, the intercepting is performed in a plurality of intermittent radiation sessions.

According to an aspect of some embodiments of the present invention there is provided a monitoring apparatus configured for detecting a change in a thoracic tissue fluid. The monitoring apparatus comprises a probe configured for intercepting at least one reflection of an electromagnetic (EM) radiation from at least one thoracic tissue of a patient, a processing unit configured for detecting a change in thoracic tissue fluid content of at least one thoracic tissue by analyzing the at least one reflection, and an output unit configured for outputting a notification indicating the change. The probe and the processing unit are configured for respectively performing the intercepting and the analyzing in at least one radiation session during a period of at least 24 hours, the at least one reflection being changed as an outcome of at least one thoracic movement during the period.

Optionally, the patient is ambulatory; further comprising an attachment unit configured for attaching the monitoring apparatus to a thorax the patient.

Optionally, the monitoring apparatus is substantially stationary, the at least one radiation session being performed while the patient is in a monitoring position.

Optionally, the monitoring apparatus is a home medical device configured for performing the at least one radiation session outside a healthcare institution center.

Optionally, the at least one thoracic tissue comprises at least one pulmonary tissue and the detecting is based on a member of a group consisting of: an accumulation of the thoracic tissue fluid content, a dispersion of the thoracic tissue fluid content, a concentration of the thoracic tissue fluid, and a composition of the thoracic tissue fluid content.

Optionally, the monitoring apparatus comprises comprising a dosage interface configured for instructing a dosage unit to dispense at least one medicament to the patient according to the notification.

Optionally, the monitoring apparatus comprises comprising a mechanical interface configured for controlling the actuation of a medical valve according to the notification.

Optionally, the output unit configured for communicating with a medical device for examining the breathing volumes of the patient, the processing unit being configured for performing the detecting according to the breathing volumes.

Optionally, the processing unit is configured for detecting a pathological indicator according to the change, the output unit being configured for generating the notification in response to the pathological indicator.

Optionally, the monitoring apparatus comprises comprising an adjustment unit for receiving adjustment information related to the patient, the processing unit configured for performing the detecting according to the adjustment information.

Optionally, the processing unit is configured for evaluating at least one dielectric related property of the at least one thoracic tissue of the patient, the analyzing being performed according to the at least one dielectric related property.

Optionally, the monitoring apparatus comprises comprising a posture detection unit configured for detecting at least one posture of the patient, the processing unit configured for detecting the change according to the at least one posture.

Optionally, the processing unit is configured for identifying a difference between a first portion of the reflection and a second portion thereof, the first and second portions being captured respectively from first and second areas of the at least one thoracic tissue, allowing the processing unit to use the difference for performing the detecting.

More optionally, the processing unit reduces an affect of a member of a group consisting of: a posture change, a change in placement, a change in the power of the EM radiation, and a change in the frequency of the EM radiation according to the difference.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a method for monitoring pulmonary interstitial fluid in the lungs of a patient, according to some embodiments of the present invention;

FIG. 2 is a graph of sectional waveforms of a reflected signal that is based on the electromagnetic waves which are reflected from the pulmonary tissues;

FIG. 3 is a schematic illustration of a method for monitoring the pulmonary fluid level during the daily and/or hospitalization routine of a monitored patient, according to some embodiments of the present invention;

FIG. 4 is a schematic illustration of a chest wall model comprised of the tissue layers, according to some embodiments of the present invention;

FIG. 5 is a graph that depicts the signal reflected from the chest wall as a result of an emission of an electromagnetic pulse, according to some embodiments of the present invention;

FIG. 6A is a flowchart of a method for monitoring a thoracic tissue, for example using the monitoring device which is depicted in FIGS. 1 and 3, according to some embodiments of the present invention.

FIG. 6B is a flowchart of a method for monitoring a thoracic tissue with respect to a posture of a user, according to some embodiments of the present invention;

FIG. 6C is a flowchart of a method for monitoring a thoracic tissue with respect to the placement, misplacement and/or disengagement of a biological probe, according to some embodiments of the present invention;

FIGS. 7A-7C are graphs of an impulse response of exemplary reflected electromagnetic waves;

FIG. 8 is a graph of a the estimated lung dielectric coefficient extracted analyzed from the reflected electromagnetic waves that depicts a number of changes of postures in an exemplary measurement;

FIG. 9 is a schematic illustration of a system for monitoring changes of fluid content in the thoracic tissue of a patient, according to some embodiments of the present invention;

Figure 10:
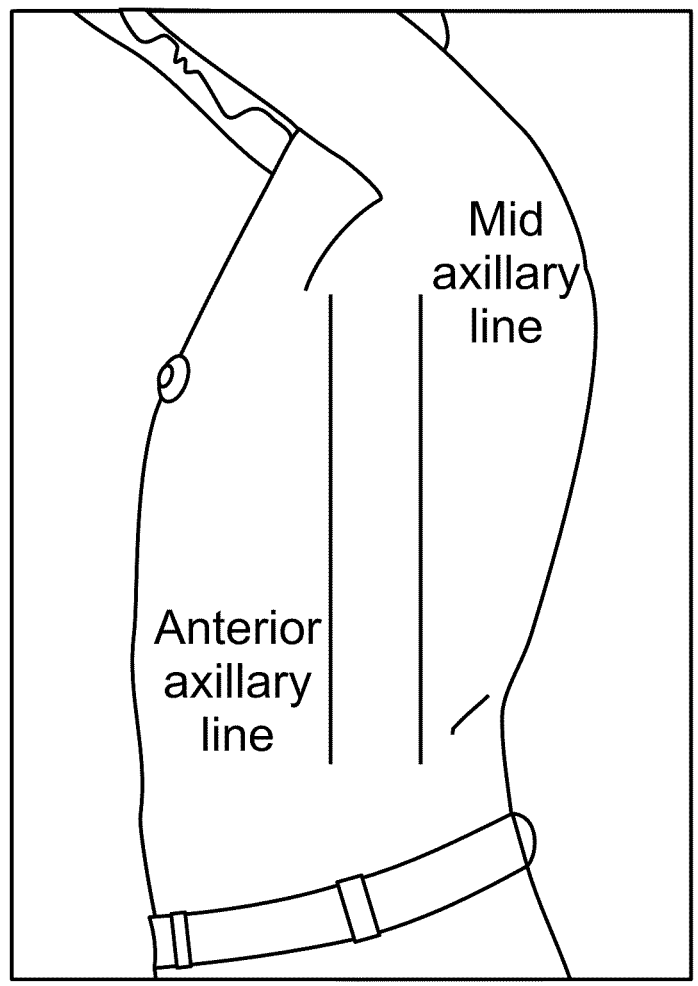
Figure 11:
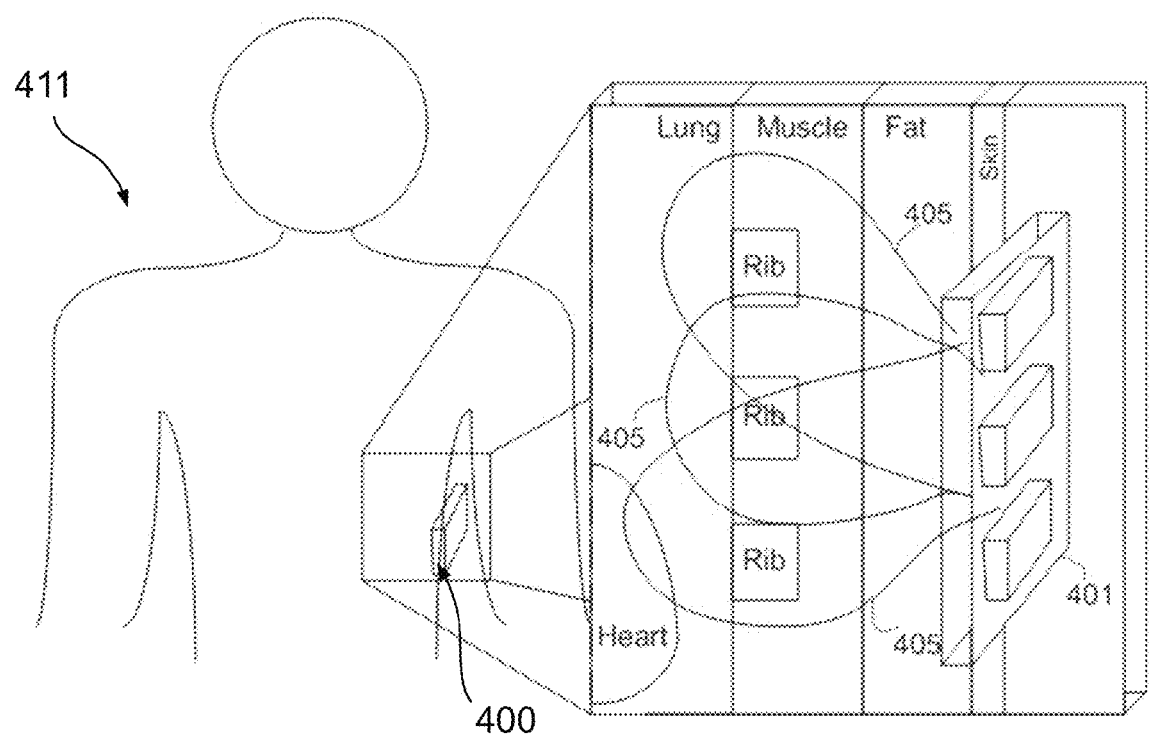
Figure 12:
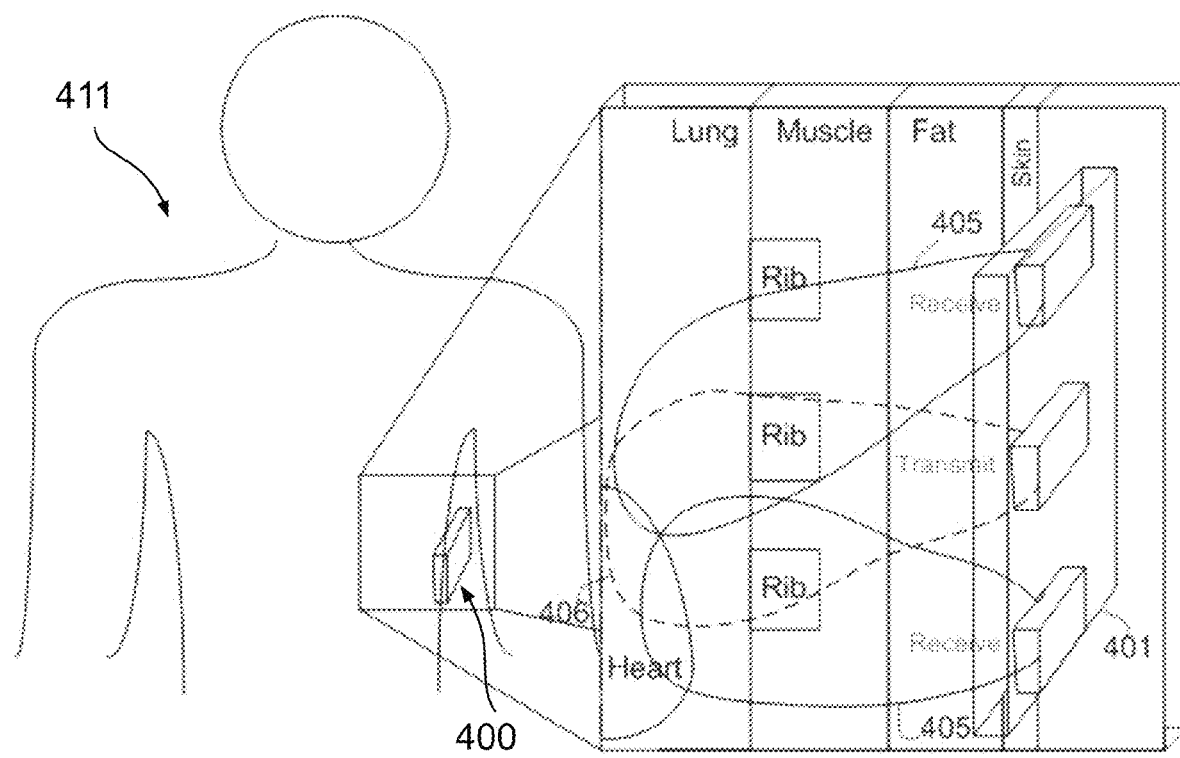
Figure 13:
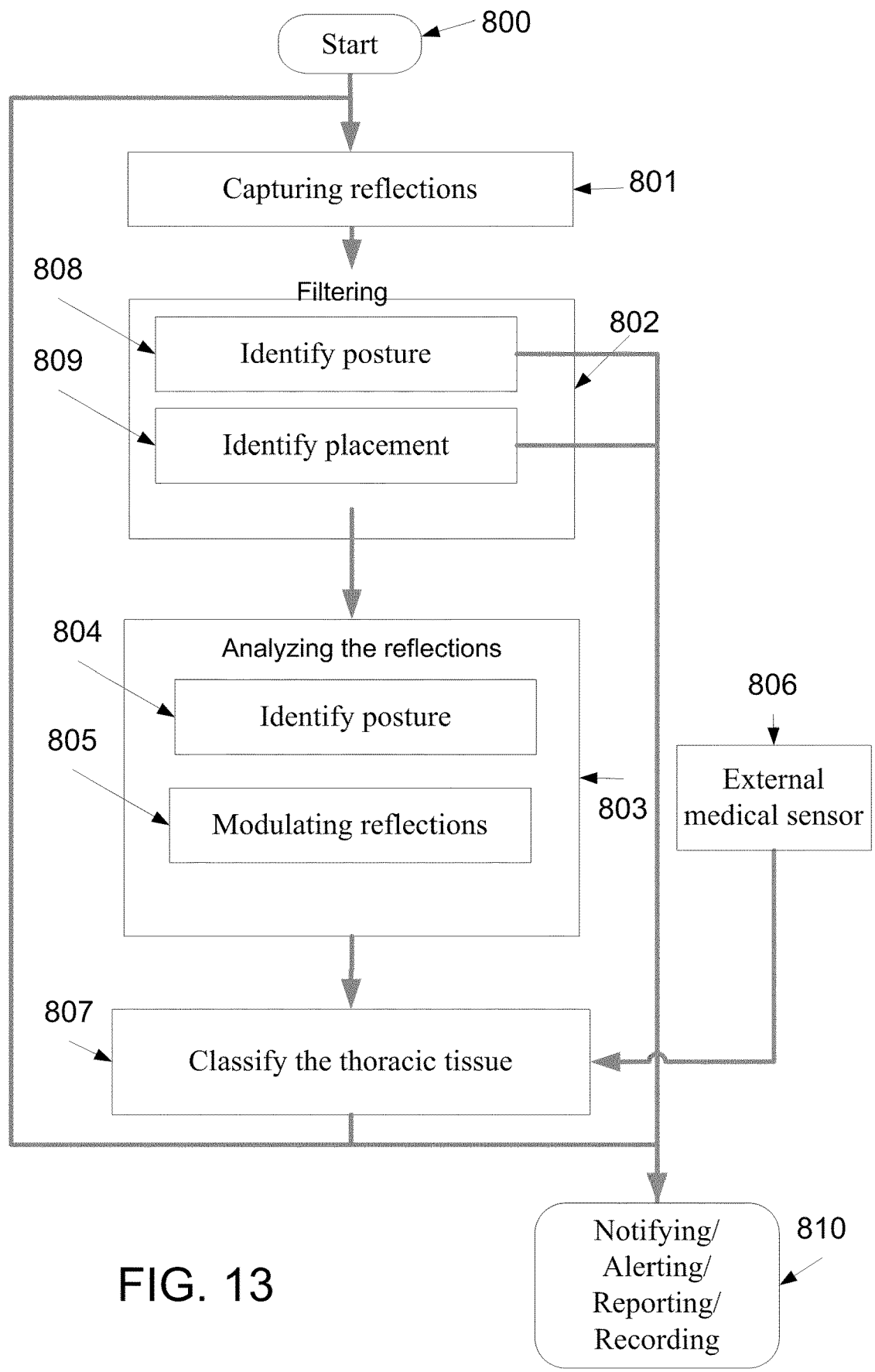

FIG. 10 is a schematic illustration of a right mid axillary line in which the wearable monitoring apparatus may be positioned, according to some embodiments of the present invention;

FIGS. 11 and 12 are schematic illustrations of a wearable monitoring apparatus with a plurality of transducers designed for beaming and/or capturing EM radiation, according to some embodiments of the present invention; and FIG. 13, which is a flowchart of a method for monitoring a pulmonary fluid level using a plurality of transducers, according to some embodiments of the present invention.

DESCRIPTION OF SPECIFIC EMBODIMENTS
OF THE INVENTION

The present invention, in some embodiments thereof, relates to a system and a method for monitoring pathological condition of a patient and, more particularly, but not exclusively, to a system and a method for monitoring pathological and/or physiological condition of a user using EM radiation.

According to an aspect of some embodiments of the present invention there is provided a method and a system for monitoring a pulmonary fluid level of hospitalized and non hospitalized patients during a monitoring period which is longer than 1, 2, 4, 8, 12, 16, 20 and 24 hours, or longer than few days, weeks, months, years. Such monitoring includes capturing a reflection of electromagnetic radiation from a thoracic tissue while the patient is ambulatory. For example, ambulatory patients may be monitored for periods which are longer than one hour, without being restricted to a certain area or to a certain activity, and immobilized patients may be monitored for long periods, for example for periods of 24 hours or more, without having to lay in a designated hospitalization room that is equipped with a stationary monitoring device. In such a manner, a hospital or a medical center may use wearable monitoring apparatuses for monitoring patients which are hospitalized in rooms which are not designated for monitoring body fluid levels.

The method comprises emitting a plurality of EM radiation and capturing their reflections from the thorax of a patient during the monitoring period. Such monitoring allows detecting a change in the dielectric related properties of at least one thoracic tissue segment, such as a pulmonary tissue, of the patient. Optionally, the monitoring allows detecting a pattern of a change in the fluid content that is indicative of a physiological, optionally pathological, condition, such as exacerbation of a congestive heart failure (CHF) patient, change of inflammatory state of an ARDS patient, dehydration, and the like.

The method further comprises outputting a time stamped measurement of the fluid content and/or a notification and/or an alarm based on historical recorded signals and computations and their analysis as will be described below. In such a manner, pulmonary edema may be treated in early stages, before the pulmonary fluid level is built up to an exacerbated pathological level and/or lethal levels.

According to an aspect of some embodiments of the present invention there is provided a wearable monitoring apparatus for monitoring pulmonary fluid level. The wearable monitoring apparatus comprises an attachment unit for attaching the wearable monitoring apparatus to the thorax of a patient during at least 24 hours, a probe, such as one or more transducers, for emitting and capturing a plurality of electromagnetic waves which are transmitted and reflected back from the thorax while the patient is ambulatory, a processing unit for calculating the pulmonary fluid level of the patient according to the reflected EM radiation and an output unit configured for outputting a time stamped measurement and/or a notification and/or an alarm according to the pulmonary fluid level to the patient directly and/or to a medical caretaker via a patient management system.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
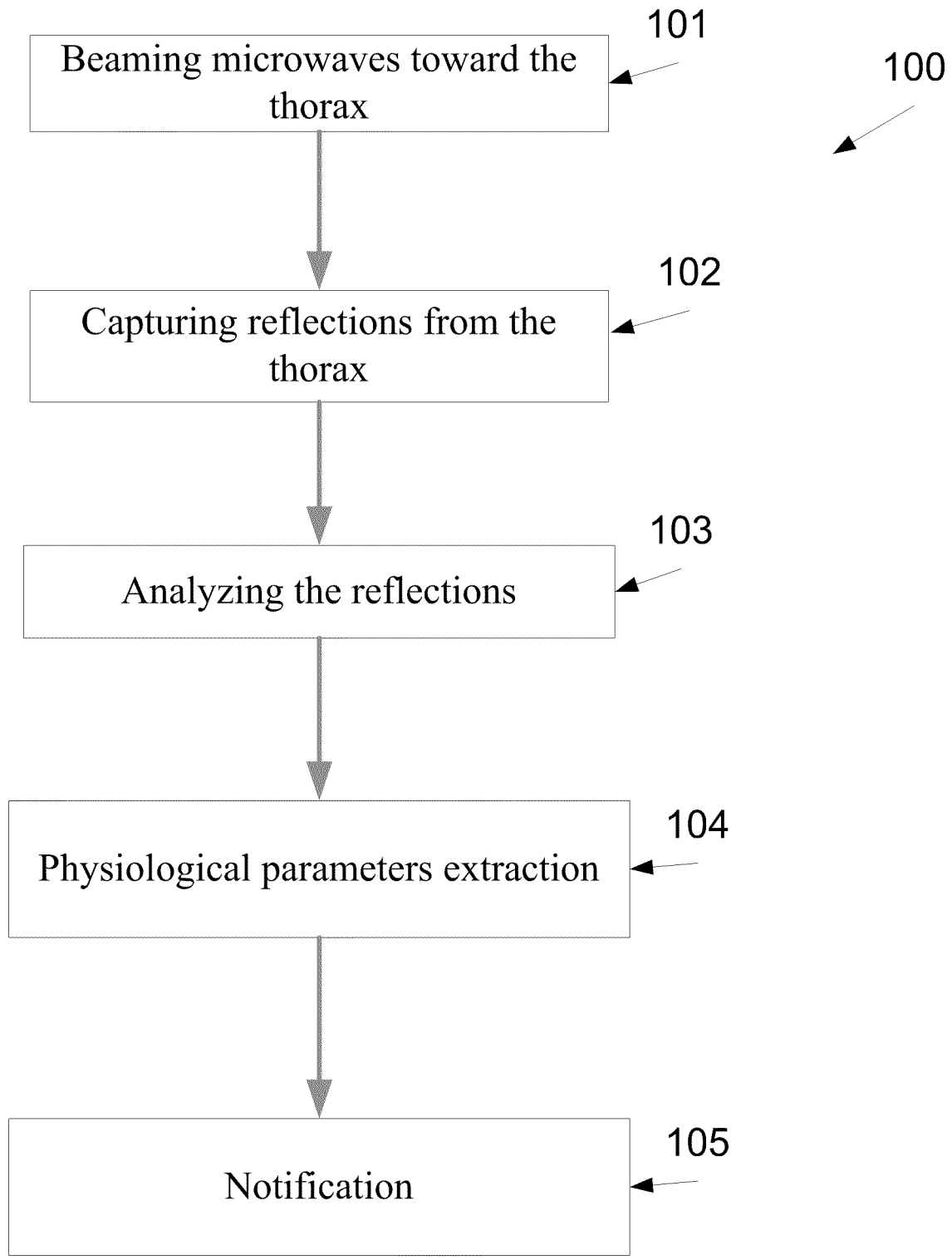

Reference is now made to FIG. 1, which is a method 100 for monitoring thoracic tissue fluids of a patient, according to some embodiments of the present invention. The method is optionally designed for long monitoring periods of 24 hours or more, for example as further described below. As such, the monitoring may be adjusted to take into account changes in the dielectric related properties of the monitored thoracic tissue, such as changes which occur as an outcome of thoracic movements.

In some embodiments of the present invention, extravascular and/or vascular lung fluids of a monitored patient are detected and/or measured by analyzing the EM properties of one or more of her thoracic tissue. A change of pulmonary fluid level, such as EVLW and/or lung's vascular fluids, which is herein measured as absolute values in milliliter (ml) and\or as a relative change, may be a result of a decompensation of a congestive heart failure (CHF) condition, and may accumulate to impair gas exchange. Such an accumulation may cause respiratory failure and referred to herein as a pulmonary edema. The change, which may be understood as accumulation and/or dispersion and/or change of distribution may be detected by analyzing changes in the reflected EM caused by changes of the regional dielectric related properties of the thoracic tissues, such as pulmonary tissues. Dielectric coefficient of a material describes its interaction with EM fields; it is represented by a frequency dependent complex number and describes the electrical permittivity and magnetic permeability of the material. Different human tissues are characterized by different dielectric coefficients. A dielectric coefficient of a thoracic tissue is affected by the dielectric coefficients of each of its components. For example, a pulmonary tissue comprises blood, lung parenchyma and air, and its dielectric coefficient is affected by their dielectric coefficients and relative concentrations. The dielectric coefficient of a tissue is determined predominantly by its fluid content. For example, a healthy fat tissue, which is of low fluid content, is characterized by a relatively low dielectric coefficient, and a healthy muscle tissue, which is of relatively high fluid content, is characterized by a relatively high dielectric coefficient. Such a dielectric coefficient may be affected by a presence of fluid, a concentration of substances, such as salts and glucose, the ratio of fibrotic tissue, and/or a concentration of inflammatory substance.

As used herein a dielectric related property of a tissue means a property that is related to the dielectric coefficient thereof. Such a dielectric related property effects the reflection of electro-magnetic radiation which is transmitted on the related tissue, such example changes the attenuation of the reflection, changes the delay which is caused by the tissue, changes the phase modulation of reflection, changes the dispersion of the radiation in the tissue.

A dielectric related property may be referred to as a region of a body and affect the dielectric related properties of it's the tissues in that region. Normal and/or abnormal processes may change the regional dielectric related property, due to a change of the composition of the volume, for example, change of fluid content as part of a degenerative process when a tissue is becoming fibrotic. A specific region may change its dielectric related property due to tissue movement and a consequent change in the configuration of tissues within that volume. The dielectric related property of a certain biological tissue may change in repetitive and/or predictable patterns according to various biological processes. For example, periodic changes may be measured along with breathing and heart cycles. Pathological processes may cause a relatively monotonous change, as occurs during the build-up of pulmonary edema.

The thoracic tissue fluid level may build up during a period of hours or days. For example, a cardiogenic pulmonary congestion is typically developed within a period of between a few hours and 30 days. Thus, in order to detect such a build up, the thoracic tissue fluid level of the patient has to be probed at least every few hours. The method that is depicted in FIG. 1 allows monitoring patients from a risk group for developing edema. The patient may be initially monitored within the hospital and sequentially be monitored outside the hospital.

The detection of thoracic tissue fluid level build up in early stages and/or the detection of critical medical condition may encourage the monitored patient to be hospitalized and/or to take a preventive treatment prior to developing a severe pulmonary edema and/or other severe medical state. Such a preventive treatment may prevent or shorten the hospitalization period of the patient. In certain medical situations, such a preventive treatment may reduce morbidity and mortality rates.

The monitoring and assessment of thoracic tissue fluid levels in a patient that is hospitalized and being treated to lower her thoracic tissue fluid levels and stabilize her condition, may help in giving more effective and safe treatment by allowing better titration of drug treatment, for example by avoiding administering of excess diuretic drugs, avoiding other more risky monitoring procedures, and/or by generating an indication that assists in a hospital discharge timing decision.

The method, which is depicted in FIG. 1, is designed to monitor the thoracic tissue fluid level of a certain patient during the daily routine or during a hospitalization period. Such a method is based on monitoring the thoracic tissue fluid level of the patient at bedside, while she changes postures, and when ambulatory Optionally, the method is implemented by a wearable monitoring apparatus, which is attached to the thorax of the patient, for example in the area marked in FIG. 10. The wearable monitoring apparatus, which may be referred to herein as a monitoring apparatus is designed to monitor the thoracic tissue fluid level and optionally to alarm the patient, to tune a dosage control unit, and/or to notify a medical center when the thoracic tissue fluid level is changed above and\or below a certain threshold and/or when the thoracic tissue fluid level is changed in an irregular and/or a pathological pace. Optionally, the monitored thoracic tissue fluid level is recorded and\or displayed to allow the presentation to the patient or the medical care giver. Optionally, the monitored thoracic tissue fluid level is recorded and may be forwarded to one or more medical centers.

First, as shown at 101 of FIG. 1, the thorax is beamed with a plurality of EM radiation. Optionally, the EM radiation is beamed from a wearable monitoring apparatus, for example as depicted in co-filed application by Amir SAROKA, Shlomi BERGIDA, Nadav MIZRAHI, Dan RAPPAPORT, Amir RONEN, and Benyamin ALMOG, entitled method, system and apparatus for using electromagnetic radiation for monitoring a tissue of a user, which the content thereof is incorporated herein by reference and referred to herein as a co filed application. Then, shown at 102, a reflection of the beamed EM radiation is captured.

In some embodiments of the present invention, the beamed EM radiation is in the range of 0.3 GHz to 20 GHz. In such a mode, time gating may be used for focusing on a specific reflection, as further described below. The shape of the pulse may be generated using different shaping techniques.

In some embodiments of the present invention, as further described below, the beamed EM radiation is narrowband waves, optionally modulated, optionally in a predefined range of frequency bands, as described in this patent and the co-filed patent.

Now, as shown at 102, a reflection of the beamed EM radiation is captured. As described above, a change of thoracic tissue fluid in a thoracic tissue, such as a pulmonary tissue is detected by detecting changes in the dielectric related properties of a thoracic tissue.

After the reflected EM radiation has been captured, analysis of the signals to extract the pulmonary fluid indicative signals, for example as shown at 103 is performed. The analysis may take into account the posture of the user and/or the placement of the monitoring apparatus which is designed for receiving the reflection from the monitored tissue, for example as described below and in the co filed patent application.

As shown at 104, the analysis allows a detection of a pathological thoracic tissue fluid content in the monitored thoracic tissue. This pathological thoracic tissue fluid content may indicates a pulmonary edema and/or a build up of thoracic tissue fluid level in a pathological pace. In addition, the analysis allows a detection of a normal thoracic tissue fluid content and/or fluid content lowering trend that indicates on an improvement in the status of a pulmonary edema condition. As shown at 105, such an analysis may be used for notifying the patient and/or medical care giver, and/or controlling a dosage unit for dispensing a medicament that is associated with the wearable monitoring apparatus, and/or controlling a medical therapeutic device such as a valve (control stage) of a ventilation machine, for example as described in the co filed application, about the thoracic tissue fluid level and/or the build up and/or build down and/or dispersion thereof. Such a notification may be used for alarming the patient and/or her medical caretaker with regard to an improvement and/or a decline in her status. Such alarming may reduce the time between the development of pulmonary edema and a treatment thereafter.

In some embodiments of the present invention, the analysis allows calculating a clinical state of a patient based on an integrative index. The clinical state is determined on a combination between the thoracic tissue fluid level and/or the thoracic tissue fluid level build up pace and vital signs and/or detected trends of vital signs which are acquired using from analysis of the reflected EM radiation and/or other medical sensors, such as electrocardiogram (ECG), myogram (EMG), an ultrasound transducer, a pulse oximeter, a blood pressure sensor, a tiltmeter, an accelerometer, and coagulometer. The integrative index is optionally scaled and/or color coded to provide intuitive follow-up of the clinical status of the patient. Optionally, the monitoring device includes an adjustment unit for receiving adjustment information related to the monitored patient from the medical sensors. In such an embodiment the processing unit is configured for calculating the fluid content according to the adjustment information.

The fluid content change pace and/or the vital signs trends are calculated from a recorded memory of previous measurements and calculated parameters of the patient. For example, as described below the pathological thoracic tissue fluid levels, which are calculated by the wearable monitoring apparatus, are recorded and used for detecting a change pace.

The clinical state of the patient is optionally calculated based on an integrative index such as described above, and other available information, for example medical history information, patient clinical condition entered by medical personnel etc., the clinical state may also be calculated based on statistical analysis of recorded information so as to adapt to the specific physiological and path-physiological characteristics of the specific patient.

In some embodiments of the present invention the wearable monitoring apparatus is associated with a dosage control unit. When the analysis allows the detection of the current fluid level and the consequent trend of fluid level, as described above, the apparatus may tune the dosage control unit to a dosage which will optimize the patient's condition. The adjustment of the dosage may be defined by the apparatus, or by the dosage control unit. The adjustment may be based on historical measurements, acquired by the apparatus, or collected in the patient management system. The dosage unit may be attached to the wearable monitoring apparatus and/or communicate therewith via wired and/or wireless connection. The medication may be taken manually or automatically using medication delivery devices. The dosage may be provided manually or automatically. Presets of dosage adjustments with respect to the measurements of the mobile apparatus may be inserted by the treating physician as well as range of allowed variations.

Figure 2:
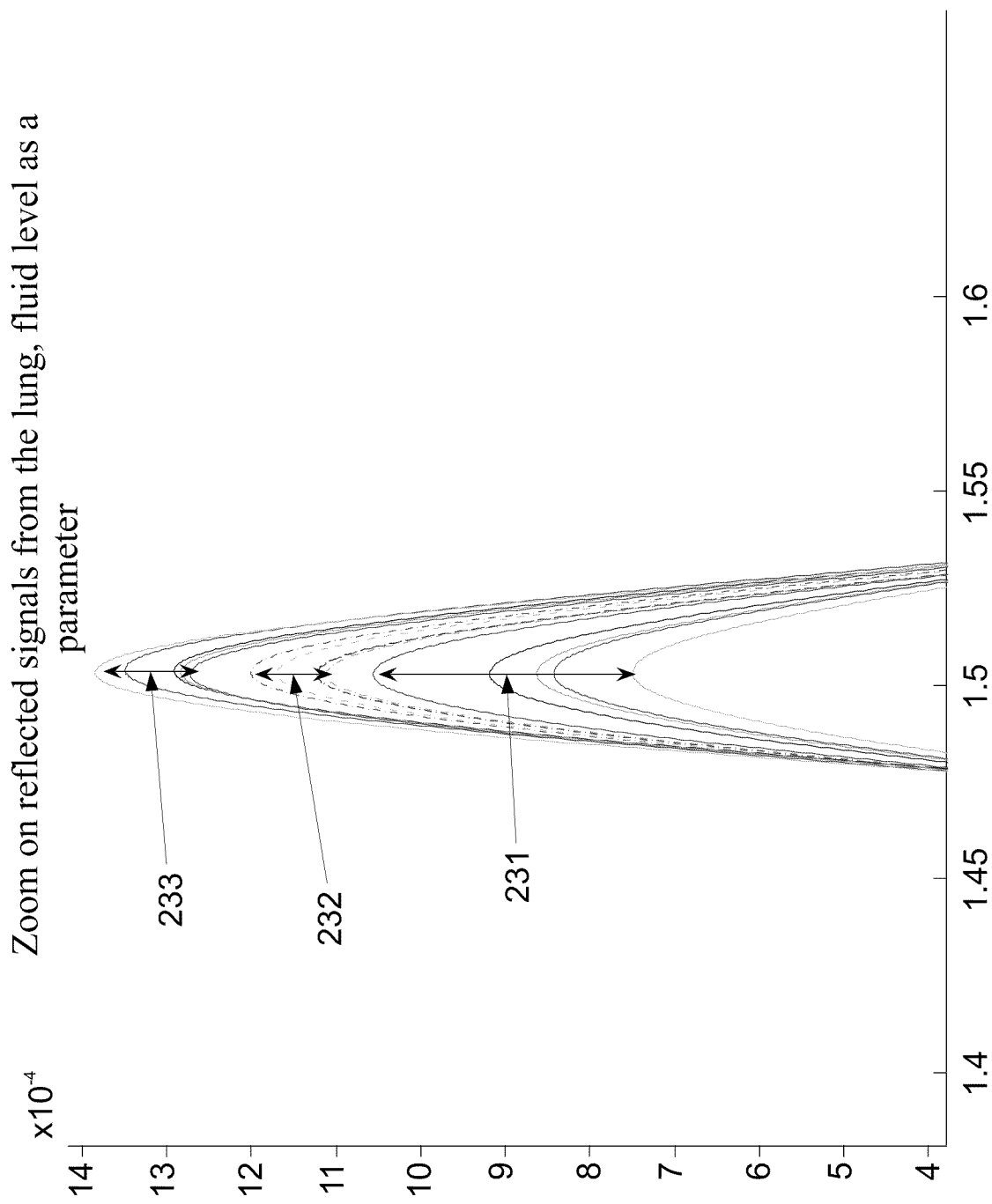

Reference is now also made to FIG. 2, which is a graph of waveforms of sections of a signal that is calculated from the EM radiation which is reflected from the thoracic tissues, such as pulmonary tissues. For brevity, a signal that is based on EM radiation may be referred to herein, in relation to analysis, filtering, segmenting, gating and the like as the EM radiation on which it is based. FIG. 2 depicts signals which are calculated from EM radiation which is reflected from healthy lungs with low thoracic tissue fluid level 231, EM radiation which is reflected from lungs with thoracic tissue fluid level of 65 mL 232, and EM radiation which is reflected from lungs with thoracic tissue fluid level of 260 mL 233. Optionally, if the EM radiation create one or more signals with a an impulse response, as depicted in range 233, the wearable monitoring apparatus generates an alarm and/or transmit a notification, for example as depicted at 105. Additionally or alternately, if the rise time of the signal section that is reflected from the thoracic tissues, such as pulmonary tissues, rise in a pathological pace, the wearable monitoring apparatus generates such an alarm. As used herein, a pathological pace is defined as any predefined pace that is indicative of relatively fast accumulation of thoracic tissue fluid level.

Figure 3:
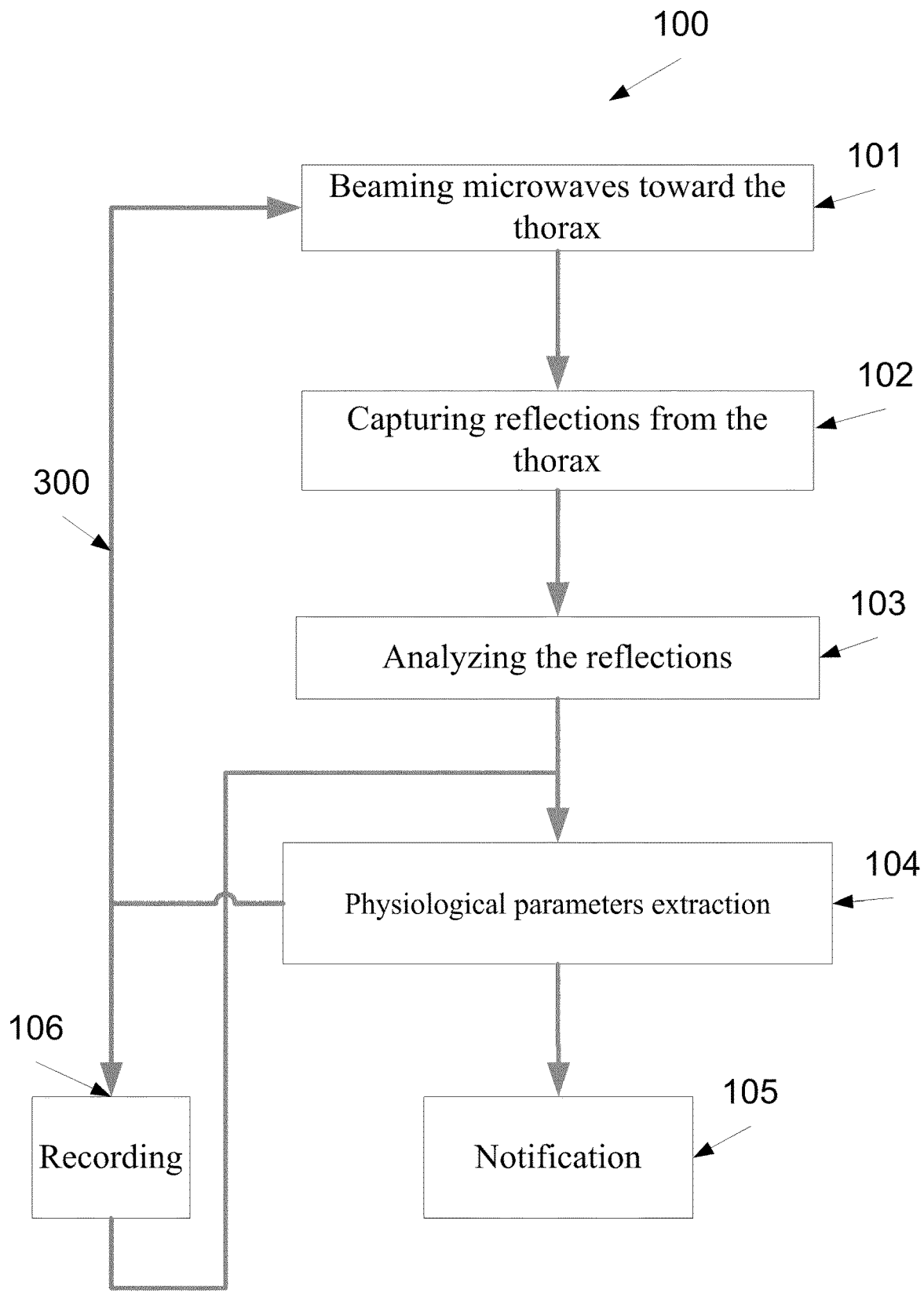

Reference is now made to FIG. 3, which is a schematic illustration of a method for monitoring the thoracic tissue fluid level during the daily and/or hospitalization routine of a monitored patient, according to some embodiments of the present invention. Blocks 101-105 are as depicted in FIG. 1. However, FIG. 3 depicts an iterative process 300 that lasts while the patient is monitored and a recording of the reflections from the thorax and/or calculations, which are based thereupon for example as further described below. Optionally, the monitoring is performed using the aforementioned wearable monitoring apparatus, which is attached to a thorax of the patient, for example as shown at FIGS. 11 and 12 below. The wearable monitoring apparatus is optionally used intermittently, for example in a number of transmission sessions during the aforementioned monitoring period. Optionally, each session lasts few consecutive breathing cycles or less. The wearable monitoring apparatus is further used for analyzing these reflections, as shown at 103, and for extracting the thoracic tissue fluid level at the thorax according to the captured reflected EM radiation, for example as shown at 104.

Optionally, the wearable monitoring apparatus is designed for monitoring the thoracic tissue fluid level of the patient by tracking changes in the electromagnetic signals reflected from the thoracic tissue or related organs. The aforementioned analysis allows the wearable monitoring apparatus to identify reflections which are originated from the lung tissue, for example according to the expected waveform pattern thereof. After these reflections have been identified, the wearable monitoring apparatus may track changes in the electromagnetic parameters by tracking changes in the respective waveform pattern. For example, relative-differential measurements may be used for measuring one or more electromagnetic coefficients of the thoracic tissue, such as a pulmonary tissue, in relation to one or more electromagnetic coefficients of references tissues which are not effected by the build up of thoracic tissue fluid level, such as the muscle, bones, and/or fat tissues. The reference tissues have electromagnetic coefficients which are relatively constant over time.

In some embodiments of the present invention, a relative differential measurement of the EM radiation, which is reflected from a transitional area between the thoracic tissue and the one or more references tissues, is calculated. These backward propagating electromagnetic waves, which may be referred to herein as transition reflections, are produced when the electromagnetic waves experiencing a change when propagated through a material or a transition of material. Significant discontinuities are expected in transitions between chest tissues like fat-to-muscle transition. The amplitude, phase and other characteristics of the transition reflections are used for estimating the parameters of a chest wall model, and calculating the electromagnetic parameters of the thoracic tissue, such as a pulmonary tissue. Optionally, the reflection of the reflected EM radiation is used as references for detecting changes in the electromagnetic parameters of the thoracic tissue.

The wearable monitoring apparatus and the method that is depicted in FIG. 3 provide a tool for continuous monitoring of the thoracic tissue fluid level of the patient. The monitoring allows early detection of exacerbation in CHF patients. The early detection allows inducing an alarm and/or triggering of a tailored titration that is part of a medical treatment. By monitoring of the thoracic tissue fluid level of a CHF patient, an early detection of a decompensation state that allows providing a treatment that alleviate the symptoms and addressing the heart functionality becomes possible. The alarming and/or the titration may allow stopping a progressive deterioration of a CHF patient before the damage to the organs of the monitored patient is irreversible.

The monitoring of the thoracic tissue fluid level of the patient may be used for monitoring various pathological processes including but not limited to degenerative processes, atelectasis, post-operative atelectasis, congestion due to acute respiratory deficiency syndrome (ARDS), trauma an infection, inhaled toxins, circulating exogenous toxins, vasoactive substances, a disseminated intravascular coagulopathy (DIC), immunologic processes reactions, a uremia, a post drowning lung fluids level, a pulmonary venous thrombosis, a stenosis, a veno-occlusive disease, a hypoalbuminemia, a lymphatic insufficiency, high altitude pulmonary edema (HAPE), a neurogenic pulmonary edema, a drug overdose, a pulmonary embolism, an eclampsia, a postcardioversion, a postanesthetic, a postextubation, and post-cardiopulmonary bypass. For example, changes in the thoracic tissue fluid level may indicate an inflammation progress of ARDS patients. In another example, postoperative atelectasis, which is characterized by the occlusion of one of the bronchial divisions followed by a collapse of a respective lung segment, is identified by the monitoring of the thoracic tissue fluid level.

Alternately or additionally, the monitoring of the thoracic tissue fluid level of the patient may be used for the early detection of CHF decompensation.

Additionally or alternatively to monitoring fluid content in patients, such as (CHF) patients, ARDS patients, dehydrated patients, and the like, the method which is depicted in FIG. 1 may be used for monitoring a dry-up process in the hospital setting, while, before and/or after the patient is going through a medical treatment. Additionally or alternatively the method may be used for guiding a medical treatment which is affected by the fluid content in a thoracic tissue, such as treatment with diuretics. Additionally or alternatively, the method may be used for managing a patient care, for example by determining the acuity of the change of the fluid content in the monitored tissue. Optionally, this acuity is used for determining the timing of medical treatments and/or the hospital discharge of patient. Optionally, this acuity is used for determining the order in which patients receive a medical treatment and/or be diagnosed.

The method which is depicted in FIG. 1, may be is employed, using wearable, stationary and/or semi stationary devices, for monitoring patient for along term of between a day and few years. In some exemplary embodiments of the present invention, the method is employed, using wearable, stationary and/or semi stationary devices, for monitoring ADHF patients. In such an embodiment, the monitoring period last at least 3 months after recurrent ADHF episodes, which optionally have been diagnosed as necessitating hospitalization. In such patients rapid decompensation is suspected within a period of 6 hours and therefore transmission sessions are performed in relatively high frequency of at least one session every hour. Optionally, each transmission session lasts approximately one minute.

Similarly, patients suffering from heart rhythm disturbances, such as tachyarrhythmia or bradyarrhythmia or heart failure patients undergoing medication modification and/or dose escalation of treatment drugs, are presumed at high risk for developing rapid pulmonary edema, and thus, monitored with similar measurement parameters along the monitoring periods.

In some exemplary embodiments of the present invention, the method is employed, using wearable, stationary and/or semi stationary devices, for monitoring patients at stress activities, such work, physical exercise and the like. In such an embodiment, longer periods of measurements and higher frequency of measurements are required. In such an embodiment, the monitoring period lasts for 3 months after an operation, a seizure, and/or hospitalization. Optionally, the transmission sessions are performed every hour. Optionally, each transmission session lasts approximately 10 minutes. Optionally, the transmission sessions are performed when medical sensors, such as accelerometer and tiltmeter and/or electrocardiogram (ECG), oximetry, and/or blood pressure sensors detect stress activities, optionally for a predefined period. The length of the measurement interval could be decreased during rest. Optionally, the frequency of the transmission sessions and/or their length is adaptive to the client clinic state and/or changed over time, for example according to a pattern of a treatment and/or expected change in the physical condition of the patient. For example, after 3 months from last hospitalization, in a stable clinical status, the frequency of the transmission sessions may be reduced to twice a day.

Optionally, the wearable monitoring apparatus is used for monitoring the thoracic tissue fluid level during and/or after a medical operation. Such monitoring allows a detection of occluded bronchus and/or other pulmonary malfunctions. The bronchus is partially or completely occluded as an outcome of different types of emboli which may be a result of a deep anesthesia depressing the coughs reflexes. For example, the wearable monitoring apparatus may be attached to patient after an operation and alert the patient and/or a medical center, for example as described below, with regard to an atelectasis process. Optionally, such an alarm allows providing the patient with treatments, such as physiotherapy, before the damage to the organs of the monitored patient is irreversible. Similarly, a wearable monitoring apparatus offering a treatment, such as sound based methods for creating a mechanical reaction, may be activated automatically. Optionally, the wearable monitoring apparatus is used for monitoring the accumulation and/or dispersion of fluids within the visceral and parietal pleura. Bleeding may be accumulated within the pleura due to a tumor, and consequently blood drainage may be conducted as part of a treatment. Monitoring such bleeding into the pleura is desired for example for proper timing of the blood drainage procedure. Similarly, heart failure patient, tend to develop pleural effusion. Thus, pleural effusion could be monitored for directing diuretics and/or drainage treatment, and for providing better assessment of the clinical condition of the monitored heart failure patient. Monitoring the accumulation of fluids in the lungs of a patient during and/or after an operation, such as cardiac operation, in which pericardial effusion may occur. The wearable monitoring apparatus may be used for an early detection of the accumulation of blood between the pericardium and the heart. Such a wearable monitoring apparatus may produce an alert to the patient and/or to the treating physician and/or center to encourage fast intervention that may prevent a risky blood accumulation.

In some embodiments of the present invention, the monitoring allows detecting pathological patterns and/or diagnosing clinical events. As depicted in FIG. 3 and described above, the patient is monitored during her daily or hospitalization routine. The monitoring optionally includes logging and time tagging the thoracic tissue fluid level, either continually or intermittently. Such logging allows using pattern recognition methods, such as multi-layered neural network and Bayesian parameter estimation for detecting pathological patterns and/or diagnosing clinical events. Optionally, the pattern detection is based on data that is received from other medical sensors and/or from an analysis of the captured EM radiation.

As shown at 106, the analyzed reflected EM radiation is documented and/or forwarded for recording by the wearable monitoring apparatus 400. Optionally, the thoracic tissue fluid levels, which are calculated as shown at 104, are recorded. Such a recording allows examination of changes in the pathological thoracic tissue fluid level along a period that lasts between few hours and few days, months, and years, for example as outlined above. The recording allows calculating one or more baselines and/or the identification of a normal range which are adjusted according to the specific patient.

Figure 6A:
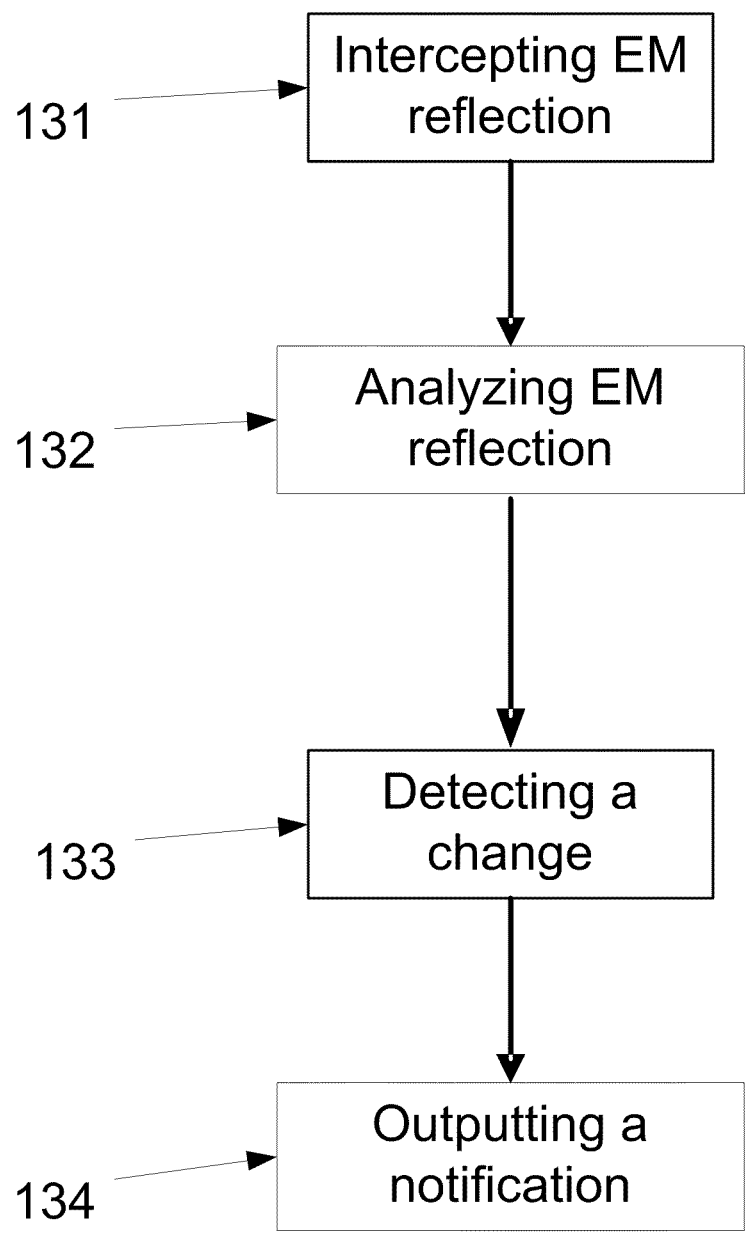

Reference is also made to FIG. 6A, which is a flowchart of a method for monitoring a thoracic tissue, for example using the monitoring device which is depicted in FIGS. 1 and 3, according to some embodiments of the present invention. First, as shown at 131, at least one reflection of EM radiation is intercepted from the monitored thoracic tissue of a patient in one or more radiation sessions during a monitoring period of 24 hours or more. The intercepting is optionally performed using the aforementioned one or more EM transducers. As shown at 132, the reflections are analyzed, for example using the processing unit which is described above. As shown at 133, the analysis allows detecting a change in the monitored thoracic tissue, for example as defined and explained above. Now, as shown at 134 a notification indicating the change is outputted, for example using a communication to a central patient management unit, as described below. It should be noted that the reflection may be changed as an outcome of one or more thoracic movements of the monitored patient, during the monitoring period. The affect of the one or more thoracic movements may be compensated according to outputs of a posture detection process, for example as described below.

Figure 6B:
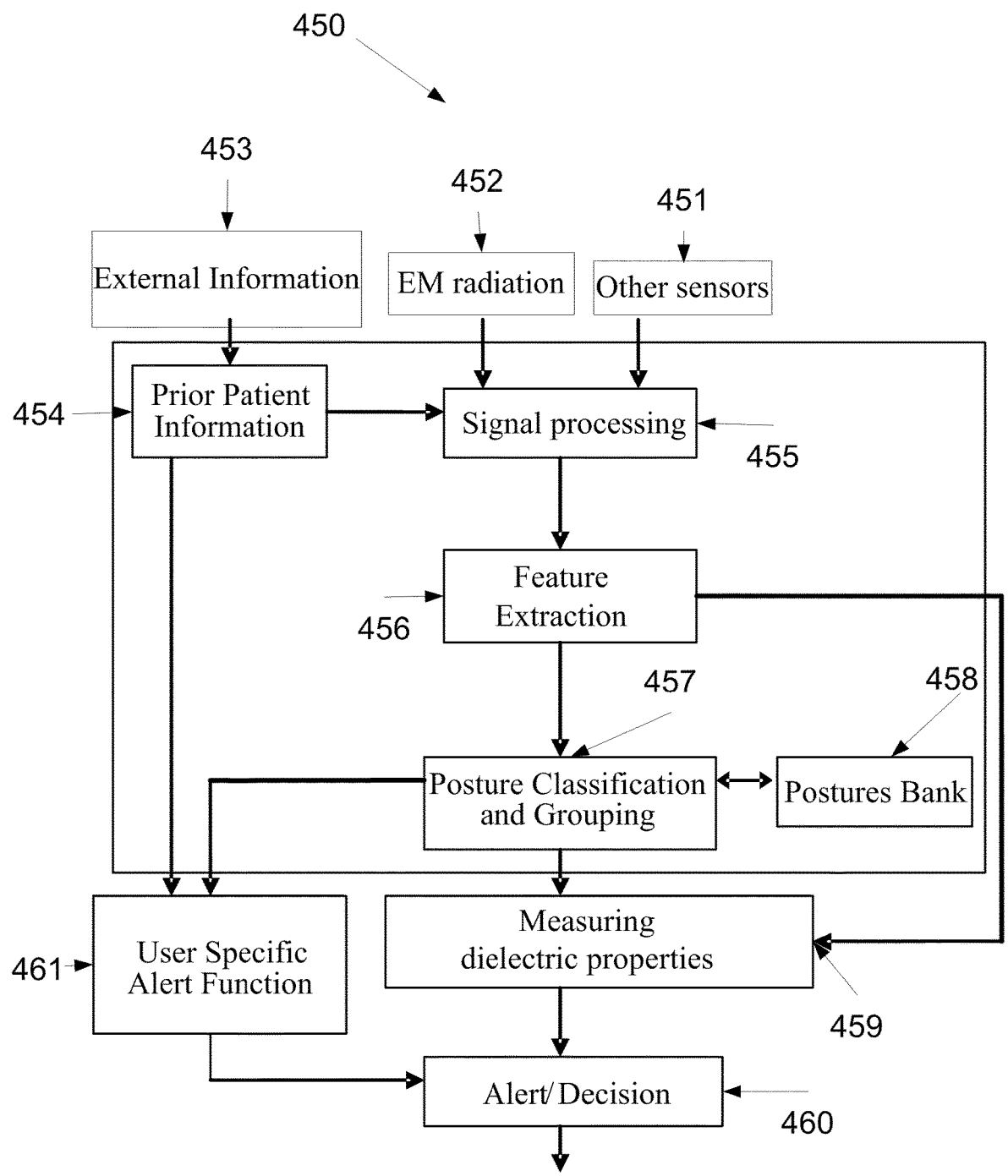

Reference is also made to FIG. 6B, which is a flowchart 450 of a method for using EM radiation for monitoring thoracic tissue with respect to a posture of a user, according to some embodiments of the present invention. This method may be integrated with the method for monitoring a thoracic tissue which is depicted in FIG. 6A, for example as further described herein.

Optionally, the monitoring apparatus is designed for identifying postures based on dielectric related properties of internal organs and/or tissues as extracted from the analysis of the EM reflected signals and/or other outputs of other sensors. In the EM-based posture detector case, posture may be defined as the relative position of the radiating element and monitored internal or external organ. As shown at 452, data from the one or more EM transducers is received at the wearable monitoring apparatus 400. Optionally, this data is acquired from the reflection which is intercepted in block 131 EM radiation. Optionally, additional data 441 from the biological probe of the monitoring apparatus and/or from external data sources 443, such medical data about the user from medical databases is gathered. As shown at 454 the medical data may be stored and/or received from the memory of the monitoring apparatus. The data 441-443 may be received simultaneously, sequentially and/or interpedently.

Optionally, the EM radiation 442, such as the aforementioned reflected signals, and the additional data 441, 443 is processed, as shown at 455 to allow the extraction of features therefrom, for example as shown at 456. A feature may be based on the morphology and/or timing of the received EM signals. For the posture detection functionality features indicative to the posture are extracted, such features may include for example the reflected signal gated to the near-antenna layers reflections, assumed to have strong posture indication. Other features are extracted for the purpose of measuring the dielectric related properties of the desired organ and used in 459. These features are indicative to the measured tissue and/or organ dielectric related properties. Some of them are sensitive to posture changes and some are more resilient. Examples of features that may be used for posture classification and acquired by analyzing reflections of EM radiations are morphologies reflections, amplitudes, positions of peak of signals from reflections of selected tissue boundaries, such as fat-muscle, lung-heart, and muscle-lung, differences of amplitudes in signals which are based on reflections and/or peak positions, either among different segments of the signal or between signals measured at different time instances, for example amplitude difference of the reflection received from lung-heart boundary in a signal measured in the time instance of contraction, compared to a signal measured in the following relaxation; or similarly for the muscle-lung boundary during end-expiratory and end-inspiratory time instances. Optionally, frequency domain features may be extracted from the EM reflection, like amplitude and phase response of a gated signal, where the gating may localize a reflection from a specific interface between tissues. In some embodiments one or more features may represent EM reflections of narrow band signals, described earlier, like phase and amplitude. Optionally, one or more features may represent information extracted from the external sensors.

As shown at 457, the extracted features may be used for classifying the posture of the monitored user. In use, the current posture of the monitored user may be found by a match between signals received from the one or more EM transducers and/or an analysis thereof and a value, a feature, a pattern, and/or a range from a posture bank 458.

Optionally, the posture bank 458 includes a scale of values, or a range of values, of exemplary features, and/or a combination of features. Optionally, the each value or range in the scale is associated with a tag of a selected posture. Optionally, during the classification the identified features are matched with the class values in the scale. The matching may be performed using known matching methods. Optionally, each class value is generated using known supervised and unsupervised learning algorithms. These matching, clustering and/or classification algorithms are known in the art and therefore not elaborated herein in greater detail.

Optionally, the posture classifier and grouping, 457, may output soft decisions like the probability of each known posture to be the current posture. Its output may be regarded as a feature for any following classifier or estimator, such as the measuring dielectric related properties block 459.

Features which are posture resilient can be used to relax the demands from the posture detector and achieve improved dielectric related properties and measurement sensitivity. Such features are required to be highly sensitive to measured tissue and/or organ dielectric related property, while being less affected by other changes like posture changes. For example, features extracted from differential signals, where differential signals are referred to as the differences between two or more signals measured during a short period of time as elaborated above.

Different postures may be identified according to their effect on the pattern of signals which are reflected from different areas in the body. In one exemplary embodiment the monitoring apparatus is used for measuring dielectric related properties of the pulmonary tissues and the extracted feature is the position of the highest peak in a differential signal based on EM radiation reflected from the thorax. In this exemplary embodiment, the position of the peak is indicative of a relative position of the muscle-lung boundary and therefore may be used for classifying the posture of the user. Optionally, the amplitude of the same peak may be used as a feature for measuring the dielectric related properties of the lung, due to its sensitivity to the dielectric coefficient of the lung.

Optionally, the posture detection based on the EM reflection from an exit boundary between tissues. This may promote the sensitivity and robustness for the measurement of the dielectric coefficient of the measured tissue due to the propagation of the EM radiation in and out the measured organ as well being reflected from a reference tissue and/or organ. For example, measuring a differential signal between the systolic and diastolic phases, and analyzing the reflection from the lung-heart interface.

The posture detector is used for reducing changes to the EM reflections due to dielectric related properties changes as a consequence of postures changes. In some aspect of the invention this functionality of the posture detection may be referred to as posture compensation. In some embodiments of the present invention the posture detection is based on a tissue model which has been adapted according to the reflection signals. Optionally, the expected reflection signal is used as a baseline and a difference between the baseline and a signal which is based on the actual measured reflections is analyzed to extract changes and/or values which are related to the dielectric related properties of the monitored tissue and/or organ. Optionally, the estimated model is calculated according to data acquired by EM sensor a non EM sensor, such as an ultrasound imager, computerized tomography (CT) and/or magnetic resonance imager (MRI). The model is a simplified one-dimensional, a two dimensional (2D), three dimensional (3D) model and/or four dimensional model and so on and so forth. The estimated model may be used for compensating for the posture effect prior to the processing of the signals 455, and/or prior to the feature extraction 456, and/or prior to the posture classification and clustering block 457 and/or the measuring of dielectric related properties 459. The model based posture compensation can reduce posture effect on some or whole of the measured reflection signals, therefore, improving posture detection statistics and reduces posture variance.

In some embodiments of the present invention, as shown at 459 and described above, the monitoring apparatus measures and/or monitor dielectric related properties of internal tissues and/or organs according to segments of a signal that is based on reflections from tissue boundaries of the monitored tissue and/or organ and/or other reference internal tissues and/or organs. These signals may be monitored over a period and/or in multiple discrete instances or in a single instance. As described above, the posture classification 457 may be used for reducing and/or removing the effect of the posture on the calculations which are based on the dielectric related properties of internal tissues and/or organs. In such a manner, alerts and/or the reports which are based on the dielectric related properties, for example as shown at 460, 461 and in block 134 of FIG. 6A, may take into account the effect of the posture of the user. In such a manner, the number of false alerts may be reduced and the reports may provide a more accurate and complete presentation of the medical condition of the user. Optionally, user specific alert are also generated according to the posture detection, for example with respect to a treatment which is adjusted for the user. In such an embodiment, the device may be used for monitoring the movement of the user and to reduce harm that the user may cause to her, to the progress of a given treatment, and/or for a monitoring process by the biological probe.

The detection of the posture of the monitored user allows taking into account the effect of the posture on the dielectric related properties of the monitored pulmonary tissue, for example by normalizing the values. For example, the analysis which is performed in block 132 may be based, normalized and/or adjusted according to the detected posture. In such an embodiment, the aforementioned biological parameters, such as clinical states, reports and/or alerts do not ignore the effect of the posture of the user on the measured clinical parameters.

In some embodiments of the present invention, the posture detection is used for guiding the monitored user to get into at an optimal, or substantially optimal, posture before and/or during a monitoring session. Optionally, the guiding may be used for instructing the user to change posture in an automatic diagnosis and/or treatment that is performed by the monitoring apparatus and/or another monitoring apparatus. Optionally, the presentation unit of the monitoring apparatus implements an interactive process during which the user tunes her posture until reaching the optimal, or substantially optimal, posture and/or moves through several postures.

Optionally, the presentation unit of the monitoring apparatus includes a minimal monitored user interface, such as a single push button and/or minimal number of audible and/or visual signals.

For brevity, all the features and embodiments which are described herein with regard to the monitoring apparatus may be used by the posture detection unit when used for detecting postures of users that wear other wearable elements and/or probed by various biological probes.

Figure 6C:
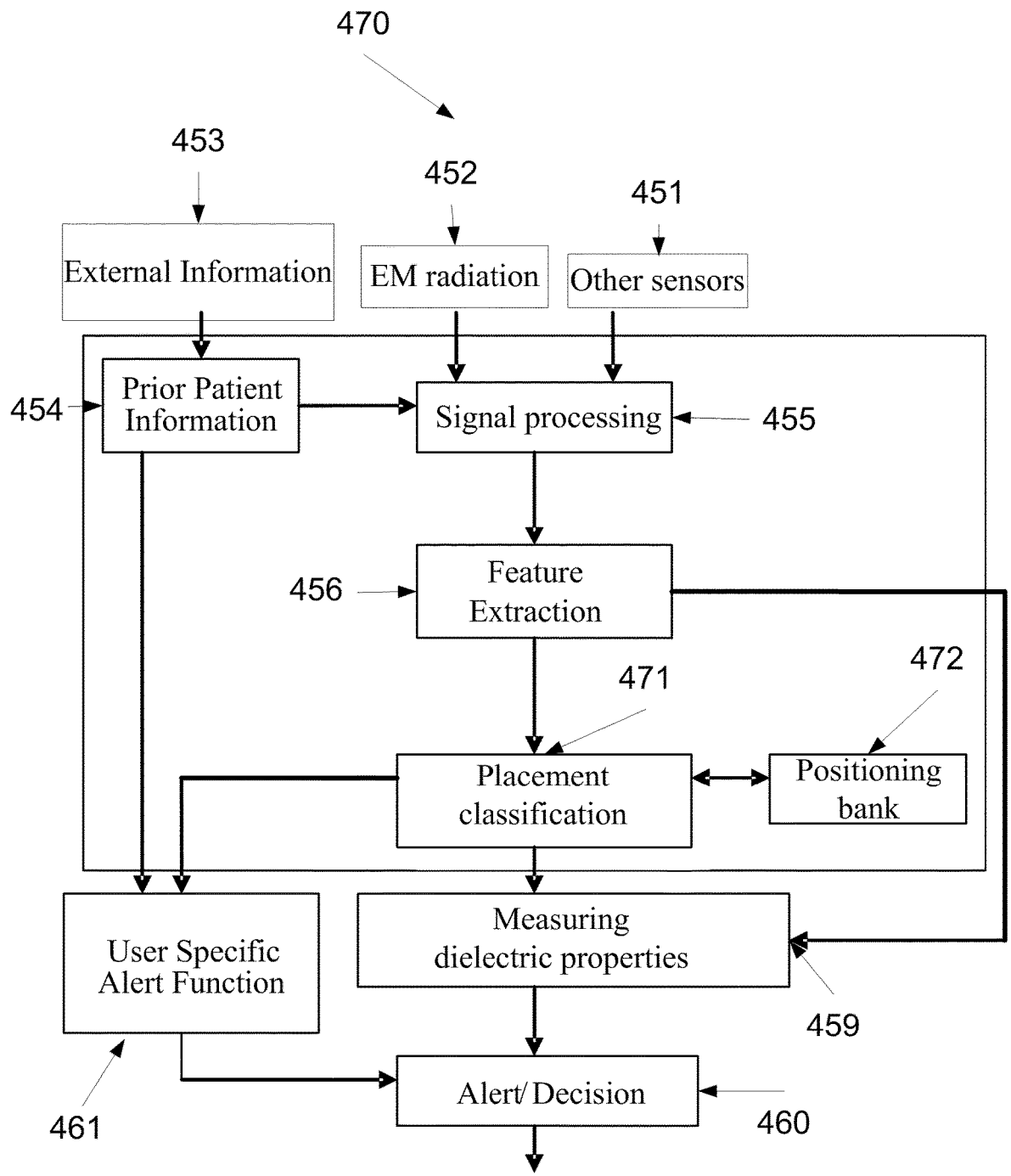
Figure 7A:
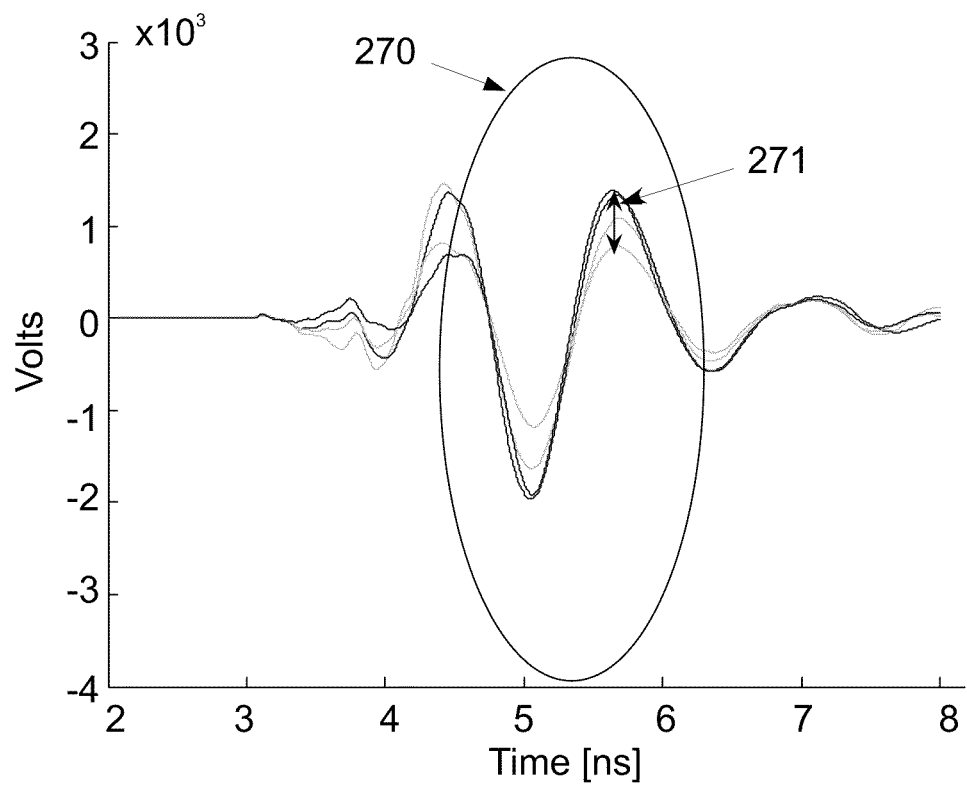
Figure 7B:
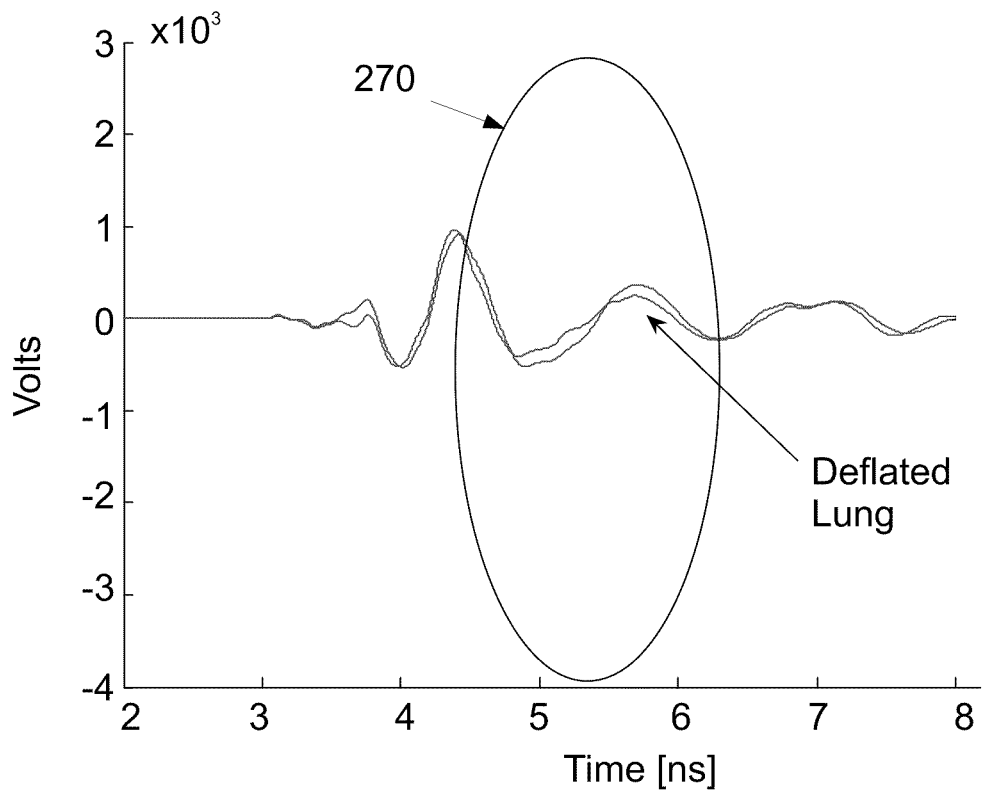
Figure 7C:
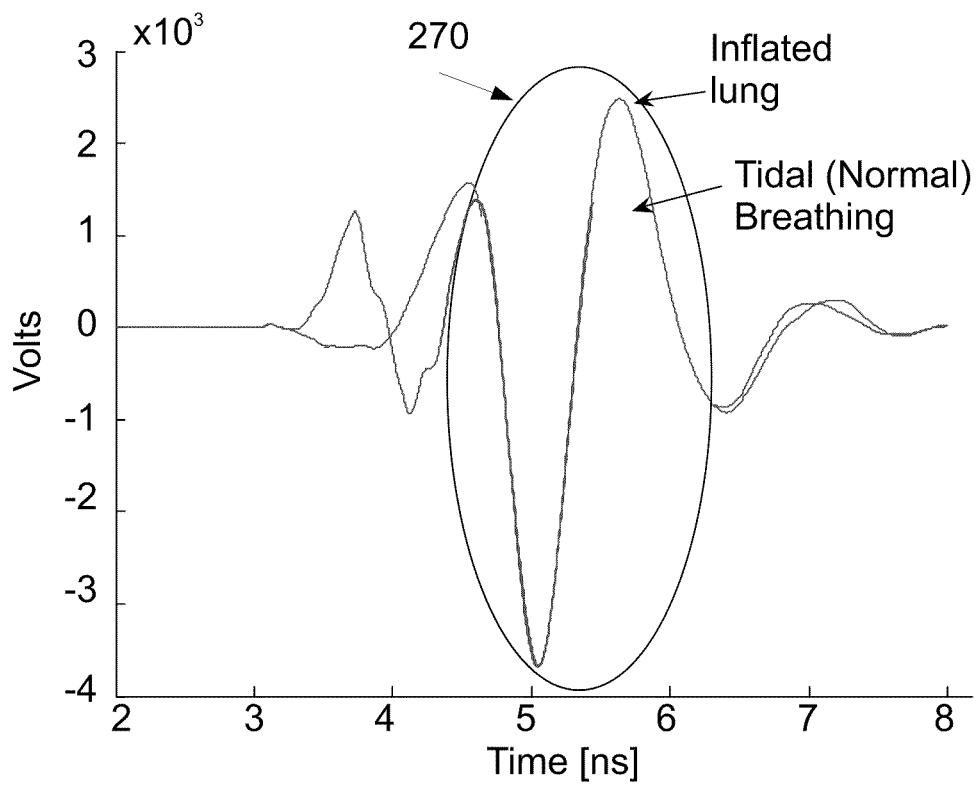
Figure 8:
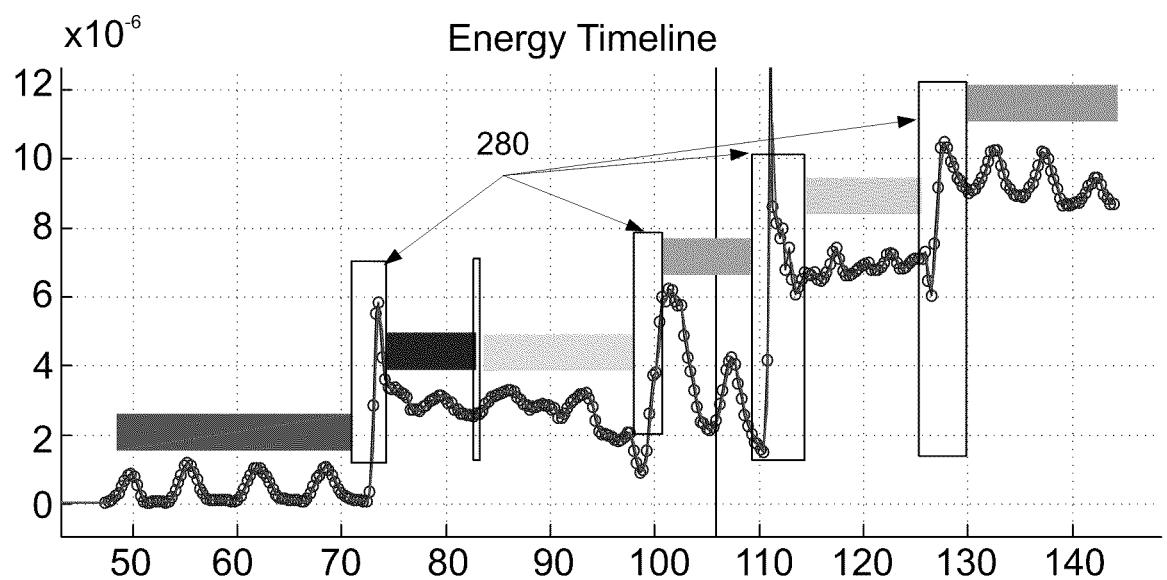

Reference is now made to FIG. 6C, which is a flowchart 470 of a method for monitoring a thoracic tissue with respect to the placement, misplacement and/or disengagement of a biological probe, such as the wearable monitoring apparatus which is depicted in the co filed application, according to some embodiments of the present invention. This method may be integrated with the method for monitoring a thoracic tissue which is depicted in FIG. 6A, for example as further described herein.

Optionally, the monitoring apparatus comprises a placement unit for monitoring the positioning of the monitoring apparatus on the body of the user. Such a monitoring allows detecting a displacement of the monitoring apparatus and/or alerting the user and/or a remote caretaker when the monitoring apparatus is displaced and/or intentionally and/or unintentionally changes a position.

It should be noted that such a placement unit may be used for monitoring placement and/or displacement of various monitoring and therapeutic devices, such as imaging modalities, for example ultrasound imaging modalities, stationary and/or mobile biological probes, and/or any other monitoring device which the positioning thereof on the body of the patient has an effect on the receptions and/or outputs thereof. In such an embodiment, the placement unit comprises a memory element, such as the memory element which is depicted in FIG. 3 and described above, for storing one or more reference values each indicative of exemplary reflection of EM radiations delivered to the monitored internal tissue of the user and/or one or more exemplary dielectric related properties. Optionally, the reference values are stored in a positioning bank, for example as shown at 472. Such reference values, which are optionally ranges of values, represent the values which are supposed to be reflected from the monitored tissue. The placement unit comprises and/or connected to one or more EM which deliver, from the monitored wearable element, EM radiation and intercept the actual reflection thereof. The placement unit comprises processing unit and/or configured to use the processing unit of the monitored wearable device. The processing unit is used for identifying and/or classifying the misplacement, placement, and/or disengagement, as shown at 471, optionally by comparing between the reference value and the actual reflection. For brevity, all the features and embodiments which are described herein with regard to the monitoring apparatus may be used by the placement unit when used for monitoring the placement and/or displacement of other wearable elements and/or biological probes.

Optionally, the placement unit is used for monitoring the initial placement of the monitoring apparatus. Optionally, the placement unit is used for monitoring the positioning in a periodic or continuous manner. In such a manner, alerts and/or the reports which are based on the dielectric related properties, for example as shown at 460, 461 and in block 134 of FIG. 6A, may take into account the effect of the positioning of the monitoring apparatus and/or the EM transducers in relation to the monitored thoracic tissues. For example, if disengagement is detected, the presentation unit of the monitoring apparatus is instructed, optionally automatically, to alert to the user and/or a medical center. This functionality enables avoiding undesired EM emissions to air and a situation in which the device is not properly coupled to the body. If the placer identifies a suspicious change in reflection it may terminate transmission sessions or reduce power to the minimum required for detecting reflections from layers which are positioned in proximity to the antenna. When the reflection from these layers matches to an expected reflection, the transmission power may be raised gradually.

The placement, misplacement and/or disengagement detection, which may be referred to herein, for brevity, as placement detection, is based on the detection of an unexpected change and/or an irregular pattern. Optionally, one or more control patterns and/or values are defined as features in 456, in order to allow the monitoring of the disengagement detection.

Optionally, the disengagement is detected when the pattern of features extracted from the received reflections from the monitoring apparatus substantially differ from the pattern of features which is expected to be received at the position of the monitoring apparatus. As described above, the monitoring apparatus is designed to be positioned in one or more areas. The configuration of the monitoring apparatus allows the user and/or a caretaker to enter the position of the monitoring apparatus. This position may be used for selecting a model, such as the aforementioned wall chest model is adapted thereto.

In such an embodiment, the disengagement is detected if the data which is received from the probe of the monitoring apparatus does not match the adjusted model.

Optionally, the disengagement and/or misplacement is detected when the data which is received from the probe of the monitoring apparatus does not express an expected physiological process, such as a breathing cycle, the pace of the heart beats, and/or any other process that have detectable effect on the backscatter of EM waves which are emitted toward the probe of the monitoring apparatus. For example, when the probe of the monitoring apparatus is attached to the chest, it is expected that the acquired signal is modulated by the breathing cycle which affects the dielectric coefficients of the lung.

Optionally, the disengagement and/or misplacement are detected when the data which is received does not match a set of reference records. In such an embodiment a set of reference records is recorded, automatically and/or manually, after a proper positioning of the monitoring apparatus. The recorded set of reference records is used for generating a reference pattern that a deviation therefrom may be used for detecting disengagement.

Optionally, the disengagement and/or misplacement are detected when the data which is received does not match a predefined range of values defined for each feature.

Optionally, the placement unit is designed to report the positioning of the monitoring apparatus and/or the accuracy of the positioning of the monitoring apparatus to a remote client and/or server, for example using the technical communication channels which are described in the co filed application.

Optionally, the placement unit estimates the quality of the positioning in reference to prior measurements recorded in memory or expected reflections. It may measure specific features and compare them to the references or the actual measurement. It then notifies the user and the algorithm of its findings.

A manual search for the correct position may include sliding the device in different directions on the body until a fixed visual and/or audible is heard. Optionally, the placement unit is connected to a mechanical adjustment unit for automatically changing the position of the monitoring apparatus, the one or more transducers thereof and/or any other biological probe, in relation to the body of the user. The mechanical adjustment unit may include an actuation unit that comprises one or more motors, gearwheels, and ratchets for automatically adjusting the extended strips, and/or any other attachment elements which are connected to the monitoring apparatus.

In some embodiments of the present invention, the monitoring is performed by placing the apparatus for short period repetitive monitoring sessions, for example a monitoring session of 5 minute measurement a once, twice, and or three times a day.

It should be noted that the posture and/or the engagement, placement, and/or misplacement processes may be used during the calculation of values which are related to intervening tissues, for example for normalizing their values.

As further described below, the pulse allows measuring the reflection from the different layers of body the monitored user. The EM radiation, which is transmitted toward the thorax of a user, penetrates tissues of a chest wall and experiences dispersion and/or attenuation. The capturing of the reflection of such EM radiation allows generating a pulse that may provide a limited spatial separation between different tissues, especially between internal tissues, such as between the pulmonary tissues and the muscle tissues. Optionally, the pulse is shaped to emphasize the boundaries of different layers which are spatially close to one another.

Optionally, the EM radiation and/or the received pulse are manipulated to improve the spatial resolution of the internal layers, thereby to improve the separation in time and space between the layers. Optionally, the transmission spectrum provides more power for higher frequencies in order to compensate for a high absorption of transmitted EM radiation with these frequencies in the internal tissues, The shaping of a pulse may be done either on an analog signal form or a digital signal form thereof, either before the transmission and/or after the receiving of the EM radiation. The pulse may be shaped according to a model of the body in the region of placement, such as the chest wall module shown at FIG. 4. Optionally, the pulse is shaped according to one or more characteristics of the anatomy of a specific patient. Optionally, the shaping is based on data, such as an image, which is acquired from an external imaging modality and/or according to an adjustment of measurements which are acquired from EM radiation which is beamed toward the body of the user, intercepted and analyzed to determine a set of reference values. Alternatively or additionally, an anatomical model is reconstructed as described below and used for adapting the pulse shaping accordingly.

The characteristics optionally include data related to layer factors, such as general thickness, thickness of a fat and/or a muscle, in the path of the region of interest (ROI) of the EM radiation. For example, the pulse shape may be designed for using equalization techniques which are based on channel estimation of the thoracic wall. Optionally, multiple pulse shapes are used for reaching higher temporal and/or spatial resolution in multiple ROIs.

In some embodiments of the present invention, the method which is depicted in FIG. 1 and/or FIG. 3 is designed for monitoring fluid content of thoracic tissue in a plurality of transmission sessions which occur, optionally repetitively, during a relativity long period. For clarity, a transmission session is process during which an EM radiation is transmitted toward a monitored thoracic tissue, such as a pulmonary tissue, a reflection of the EM radiation is captured from the monitored thoracic tissue, and the fluid content and/or a change in the fluid content of the monitored thoracic tissue is calculated and/or classified. Such a method may be employed by a system, stationary or semi stationary, such as a monitoring device which is located in a hospitalization room and/or a home medical device, and/or mobile, such as the wearable monitoring apparatus which is described in the co filed application. Such a system may be referred to herein as a long-term intermittent monitoring system.

Optionally, the stationary or semi stationary system is designed to allow the user to position an EM probe in front, behind, and/or in proximity of the monitored thoracic tissue for a transmission session. Such an embodiment, allows performing long term monitoring without requiring from the user to wear a probe for long terms. For example, a user may position the EM probe and/or get into a, area which is monitored by the EM probe every 1, 2, 4, 6, 8, 10, 12 and 24 hours, days, weeks, and/or months for a transmission session that last between few seconds and few hours, optionally minutes. Optionally, a placement unit, for example as described above and/or in the co filed application, is used for positioning the probe in front, behind, and/or in proximity of the monitored thoracic tissue. In such an embodiment, the monitoring system may include a Man-Machine Interface (MMI) that is designed to guide a user, a caretaker, and/or a mechanical arm to position the probe in front, behind, and/or in proximity of the monitored thoracic tissue. Optionally, a probe placement area is marked on the body of the patient. In use, the placement unit senses the reflections from body of the user and decides on the accuracy of the positioning, optionally with reference to prior recorded measurements and/or to expected reflections. Optionally, the posture of the user is detected by a posture detection unit, for example as described above and/or in the co filed application. Changing a posture may be referred to herein as a thoracic movement. In such an embodiment, effects of the posture of the user may be cancelled or reduced, as described above and/or in the co filed application. Optionally, the posture detection may be used for determining whether the user is in a good posture for a transmission session or not or whether the measurement is reliable for further analysis. Optionally, data which has been captured during previous transmission sessions is recorded and used for the posture detection process. In such a manner, analysis based on a number of registered measurements may provide robust estimations of the pathological state.

Chest Wall Model

Figure 4:
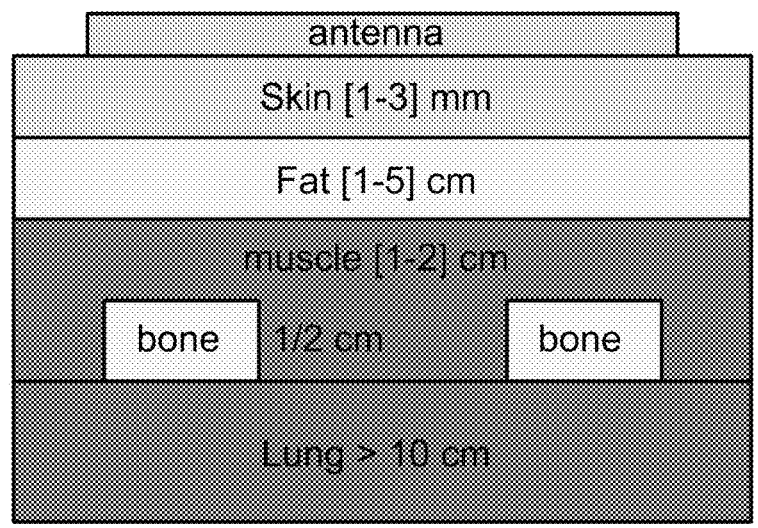

Reference is now also made to FIG. 4, which is a reference chest wall model 200 of the thorax, according to some embodiments of the present invention. The methods which are depicted in FIGS. 1 and 3 may be based on a reference chest wall model, optionally changing over time according to patient's physiology and posture and dynamical periodic processes, such as a human body tissue dielectric model. Such a reference chest wall model may be used as a reference for modeling properties and/or a range of properties for evaluating deviations in the level and/or build up pace of the thoracic tissue fluid level. Optionally, the reference chest wall model is used for analyzing reflections from the thoracic tissue, such as a pulmonary tissue.

Optionally, for example as shown at 200, the reference chest wall model 200 maps expected dielectric coefficients of tissues of an exemplary reference model of EM properties of tissues of a thorax section. For example, the model at FIG. 4 includes the following layers with the following possible thicknesses:

a skin tissue layer (1-3 mm);
a fat tissue layer (50-500 mm);
a muscle tissue layer (50-200 mm);
a bone layer (30-60 mm); and
a pulmonary tissue, layer (~100 mm).

For some or all the layers, the reference chest wall model includes one or more of the following parameters:

a relative dielectric coefficient;
thickness, for example as described above;
an estimated signal shape; and
an equivalent frequency response of a layer capturing an effect imposed on an RF signal that is propagating in it, for example estimation of the attenuation and dispersion of a pulse which propagates through the respective layer.

In some embodiments of the present invention, the reference chest wall model is dynamic. In such an embodiment, the reference chest wall model may have time dependent parameters. Optionally, the parameters of the reference chest wall model are changed in a circulatory manner that is adapted to a predefined cycle, such as the breathing cycle. The dielectric coefficient of the lungs is dependant on the fluid content of the thoracic tissue and on volume of the lungs. Thus, the dielectric coefficient of the lungs may vary during the breathing cycle of the patient. Optionally, the reference chest wall model is adjusted according to a general breathing cycle. Different patients may have different breathing cycles. The physiological condition of a patient has an effect on her breathing cycle. For example, the gender, the weight, the age, and/or the condition of the lungs affect the breathing cycle. Optionally, the reference chest wall model is adjusted according to a breathing cycle that is adapted to the monitored patient.

Optionally, the parameters of the reference chest wall model are changed according to dynamical changes of regional dielectric related properties which may be attributed to other biological processes, such as pathological and/or recovery processes, for example as an outcome of compensatory mechanisms, medication treatments, and/or infections. These processes may develop in various paces, thereby dictating the duration of the monitoring period and the time resolution required.

In some embodiments of the present invention, the reference chest wall model is adjusted according to the angle from which the EM radiation is reflected. As the lungs are positioned behind the costae, the angle of incidence of the EM radiation may substantially affect the properties of their reflection. Optionally, a number of reference chest wall models are generated in advance and selected according to the position of the wearable monitoring apparatus that beams the EM radiation and captures the reflections thereof. Optionally, the reference chest wall model is adjusted according to the position of the wearable monitoring apparatus.

Figure 9:
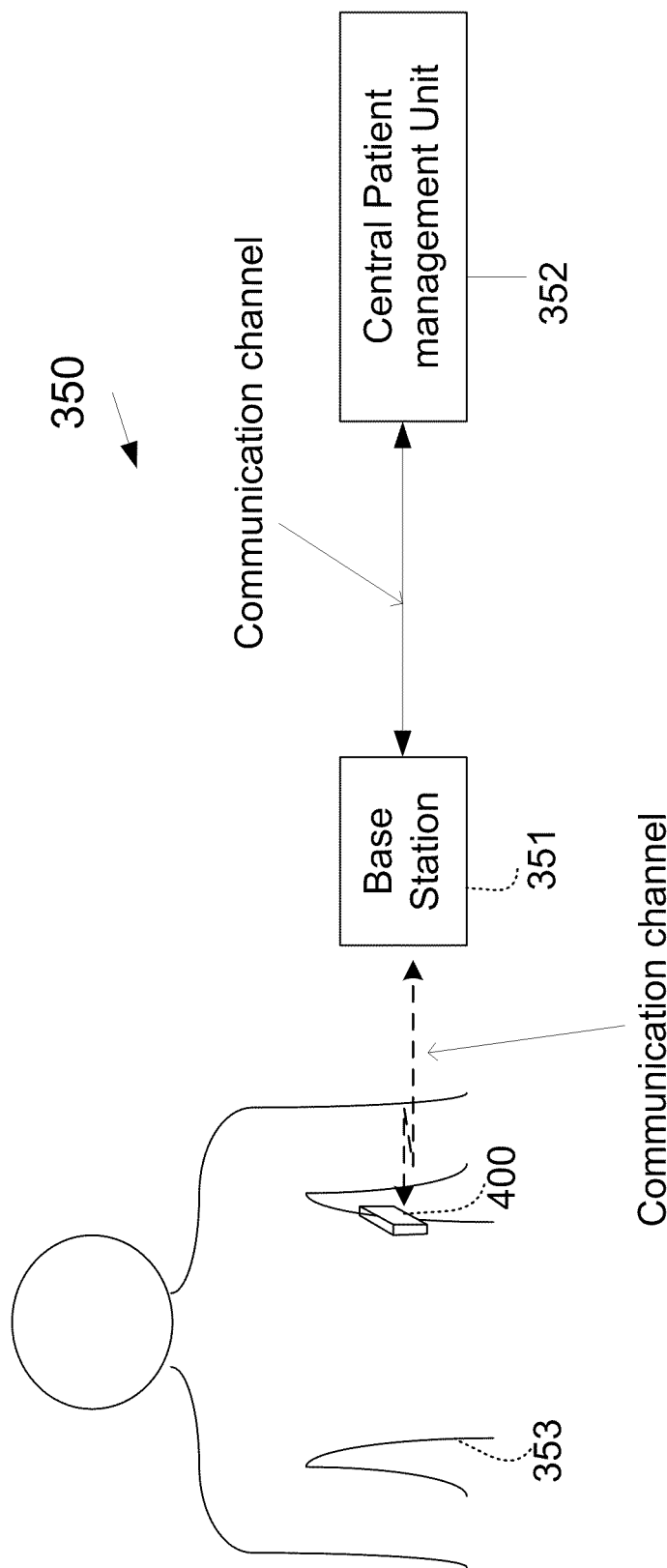

Optionally, before the reflected EM radiation is analyzed, as shown at 103, the reference chest wall model is adjusted. The adjusted model increases the accuracy of the predictions, and alters the interpretation of the received signals of expected reflections of EM radiation from different tissues of the lungs. For example, different patients may have different dielectric coefficients and/or fat layers with different thicknesses. The adjustment optionally allows adjusting the reference chest wall model according to the patient from whom the EM radiation is reflected. For example, the adjustment allows the adjustment of the reference chest wall model according to the thickness of the fat and muscle layers of the monitored patient. Optionally, the adjustment is based on medical information that is related to the monitored patient, such as the gender, the height, the weight, and the perimeter of the patient. Optionally, the wearable monitoring apparatus has a user interface (UI) that allows the inputting of the medical information. Optionally, the wearable monitoring apparatus receives the medical information from a remote clinical center and/or database, for example as described below in relation to FIG. 9. Optionally, the wearable monitoring apparatus receives the medical information from an external imaging modality, such as X-ray modality, computerized tomography (CT), Ultrasound modality and/or magnetic resonance imager (MRI). Optionally, the wearable monitoring apparatus reconstruct these parameters based on detecting transition reflections (as defined above).

Gating Adjustment and Channel Learning

As described above, the monitoring is performed by analyzing the EM radiation which is reflected from the thorax of the patient. The accuracy of the analysis is affected by the registration of the signal which is based on the isolation of a region of interest (ROI) in the signal. Acquisition of the signal in specific ROIs is performed by gating. The gating may be based on the described chest model.

Movement, Cyclic Physiological Processes, and Disturbances

Cyclic physiological processes, such as the breathing cycle and the pace of the heart beats, have detectable effects on the backscatter of EM radiation which is reflected from specific tissue layers, such as the thoracic tissue. In order to improve the monitoring and/or the detection of changes in the thoracic tissue fluid level, the effects of these physiological processes are optionally identified and used to improve the analysis. Thus, it may be used for posture detection and physiological parameter extraction as elaborated above and described in the co filed application.

The breathing may be detected by first identifying the breathing frequency by analyzing the reflected signals in the frequency domain looking for the peak value in the physiological range, followed by tracking each respiration cycle in the time domain signals. Thus, both the frequency and the dynamical volumes may be estimated.

Optionally, the reflections from the thoracic tissue, such as a pulmonary tissue, are adjusted according to breathing cycle of the patient, for example as described above. Optionally, the breathing cycle is defined by the respiration rate, respiration depth, and/or an estimation of the respiration output of the patient. The breathing cycle may be based on the output of various sensors and/or methods, including not limited to electrocardiogram (ECG), oximetry, and/or blood pressure. These sensors may be mounted within the apparatus or may wirelessly communicate with a remote component of the system, for example as described below.

In some embodiments of the present invention, a tracking algorithm is used for compensating for relative movements of the antenna in respect to the reflections points of interest, where such reflections are in some embodiments are indicative to lung fluid content. Other changes which are not movements may be compensated as well, for example, physiological changes such as skin sweat, or changes in the measuring apparatus parameters like transmitter power or receiver noise-figure. A tracking algorithm may use a certain signal or a pattern, such as the fat-to-muscle transition, as a reference signal. Thus, for example, a reflection from the fat-to-muscle transition may be used for tracking changes during breathing cycles or other posture changes and can be detected by signal analysis methods.

As depicted in FIGS. 11 and 12 the wearable monitoring apparatus may include number of transducers. In such an embodiment a space diversity method may be employed for reducing the effects of fading by the simultaneous use of two or more of the number of transducers, preferably separated from one another by one or more wavelengths.

Such an embodiment allows higher spatial resolution by creating a focused beam that is emitted in desired directions. Moreover, such an embodiment may allow increased ability to localize transition reflections by source separation methods as used in ultrasound based methods.

Figure 5:
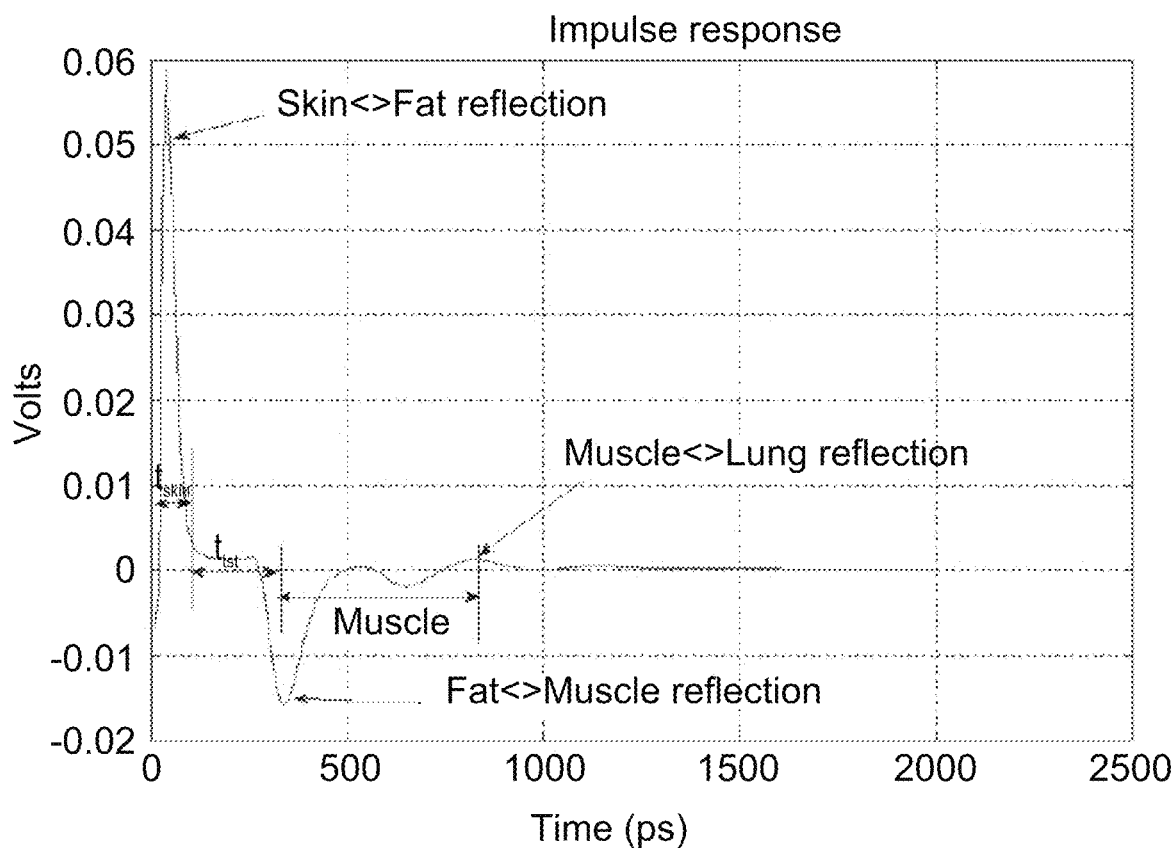

As shown at FIG. 5, the intensified reflections are received from low-depth transitions between the antenna and the skin or between the fat layer and the muscle layer. These reflections may be used as references while the reflections from the main interest area are analyzed for determining the thoracic tissue fluid level.

Optionally, the method which is described in FIGS. 1 and 3 includes identifying and factoring out distortions and noises that affect the relative amplitude of the waveform of the reflected EM radiation. Examples for such distortions are changes in the transmission (TX) power, changes in the match between the antenna and the skin face, background noise, and the like. The distortions and noises may be factored out using a number of transducers, for example as described below.

Additional devices such as an accelerometer or a tiltmeter may provide additional data for classifying the current posture and/or activity level of the monitored patient.

Optionally, the method which is described in FIGS. 1 and 3 is implemented by a wearable monitoring device, such as the wearable monitoring device which is described in the co filed application. Optionally, wearable monitoring device communicate with a patient management unit and/or a medical center, for example as described in the co filed application. Optionally, wearable monitoring device uses one or more transducers, for example as described in the co filed application.

In some embodiments of the present invention, the wearable monitoring apparatus 400 is configured to match the physical condition and/or medical history of the probed patient. Optionally, the configuration is performed, either automatically and/or manually, after the wearable monitoring apparatus 400 is attached to patient's body. Optionally, a configuration process is associated with the initial placement of the wearable monitoring apparatus 400. The automatic configuration may be based on immediate measurements and\or model estimation. Thus, allowing for example the definition of the gating parameters accordingly. Optionally a semi-manual configuration process is used where the patient and/or the treating physician are required to enter medical data and/or to select a monitoring pattern and\or define various thresholds for notifications of either the medical treating team and/or the patient.

For example, the patient and/or the treating physician are required to enter one or more of the following initial parameters:
1. The age of the patient.
2. A medical condition and the severity thereof.
3. One or more physical measurements, such as weight, height, and an approximation of a chest diameter.
4. A monitoring positioning—the wearable monitoring apparatus 400 may be placed in several positions in relation to the patient's thorax. Optionally, the configuration process includes a manual and/or automatic sub process wherein the position of the wearable monitoring apparatus 400 is defined or selected. A location for positioning the apparatus may be selected such that the thoracic tissues, such as pulmonary tissues, are detectable during the entire breathing cycle. For example, the position may be in front of the fifth and sixth ribs, at the right mid axillary line, for example as shown at FIG. 10. It should be noted that positions in which the lungs wall is monitored in portions of the breathing cycle may also be selected.

One or more pathological indicators, such as alarm thresholds, as used. These thresholds may be defined with regard to the other initial parameters. The thresholds are defined automatically and/or manually. Optionally, automatic threshold levels are defined during the configuration of the device and may be adjusted during monitoring, either manually and\or automatically by the system. For example, the physician may change the automatically set threshold after medication dosage adjustment to be notified of possible effects.

The configuration parameters may be entered, automatically and/or manually by the wearable monitoring apparatus 400 and/or the base station 351. Optionally, the patient may follow a configuration instruction set. Such a set may require a physical activity, such as 6 minutes walk, deep breathing, and the like.

Optionally, the output of one or more other wearable monitoring apparatus and/or sensor may be examined during the adjustment process. For example, a spirometry device may be used for examining the lungs capacity in conjunction with the thoracic tissue fluid level monitoring. The outputs of the spirometry device may be used for adjusting the breathing volumes and to provide an absolute scale for estimating the level of the edema.

Optionally, the thoracic tissue fluid level monitoring is performed as a clinical follow up of a treatment that is managed by a clinician. For example, a treatment which is given to a patient who has been hospitalized with relatively high level of edema may be monitored using the wearable monitoring apparatus 400. At the end of the treatment, the patient is monitored to detect a possible exacerbation. The alarm threshold may be determined by the clinician, for example according to his experience therewith.

Optionally, the wearable monitoring apparatus 400 is designed for verifying the positioning thereof in relation to the thorax. Such verification may be performed by matching the received signal with the tissue model. Optionally, a feedback is given to the user and\or the treating medical team or a centralized IT center, for instance by a using LED and/or alarm or any other indication.

In some embodiments of the present invention, the wearable monitoring apparatus 400 comprises a user interface (UI) for allowing the user to adjust the monitoring process, for example as in the co filed application, and/or for presenting, either audibly and/or visually, notifications to the user. The notifications optionally include audio notifications, one or more blinks, and/or vibrations. The wearable monitoring apparatus 400 may present, automatically and/or upon request, the thoracic tissue fluid level and/or any medical indicator and/or trend. For example the UI may present a congestion level together with the respiration depth and rate and heart rate. As described in the co filed application, the UI may be used for generating and presenting an alert.

Such notifications may not be limited to the wearable monitoring apparatus 400 and optionally presented, concurrently or intermittently, at the base-station 351 and/or the central patient management unit 352. Alternatively, the notification and the presentation of the medical data can be integrated in external devices such as medical monitors and\or PDA used by the medical team.

Reference is now made to FIGS. 11 and 12, which are schematic illustrations of a wearable monitoring apparatus 400 with a plurality of transducers for beaming and/or capturing EM waves, according to some embodiments of the present invention. FIG. 11 depicts a wearable monitoring apparatus 400 with an array of transducers 401 that is designed for transmitting EM signals capturing its reflections from a plurality of different directions. FIG. 12 depicts a wearable monitoring apparatus 400 with an array of transducers 401 that includes separate transducers for capturing reflections from the tissues 405 and separate transducers for transmitting EM waves toward the tissues 406. The different elements may be located in proximity to one another or spread over different locations, in a similar manner the elements can have the same pointing direction or can have different pointing directions. For example, one antenna element may be placed on the back of the user, another on the side and third on the front of the user thorax. In the group of antenna elements which are depicted in FIGS. 11 and 12 the relative phases of the respective signals feeding the antenna elements are varied in such a manner that the effective radiation power of the phased-array is reinforced in a specific internal area of the user's body, for example in the pulmonary tissues of the user 411, and optionally suppressed in other directions. In an equivalent manner, the phases of the received signals from the different antenna elements may be combined to focus the elements on a specific internal location. As described above, reflections from the pulmonary tissue may be calibrated according to the reflections from reference tissues, for example increasing the received reflected power from the muscle-to-lung interface, by increasing the inflate-deflate differential signal on the lung gating. Any or all of the transmission and/or reception of the EM signals can be adjusted jointly or separately to maximize the described lung reflection.

By using multiple transducers the time/space separation may be improved. For example, different antenna elements are designed to be focused on reception and/or transmission in different directions, where the interception of the transmission and reception areas of focus are strongly emphasized respective to other areas, so as to improve isolation from internal weaker signals from strong reflection which may or may not overlap in time.

Optionally, the array of transducers 401 comprises transmitting and intercepting antenna elements. By separating between transmitting and intercepting antenna elements, transmission and reception isolation is increased. The improved isolation increases sensitivity to weaker reflections from inner tissues and/or organs, by reducing the reflections received from layers which are in proximity to the transmitting antenna elements. Reception of strong reflections from the first layers in proximity to the transmitting antenna elements, such as skin and fat, are reduced or eliminated in separated receiving antenna elements, therefore achieving improved sensitivity to weaker signals from deeper layers.

The separation of different reflection according to reflected areas allows overcoming microwave monitoring difficulties. For example, when two or more reflections from different areas are simultaneously, or substantially simultaneously, but overlap in time of reception, physiological phenomenon may be masked for example due to mutual cancellation. Focusing the reception and/or transmission to different areas may isolate the two or more reflections from each other and enable efficient extraction of the physiological phenomenon. Optionally, multiple antenna elements and/or multiple transducers are used to reduce irregularities, such as noises, disturbances and/or interferences, which are intercepted in part of the antenna element and/or transducers. Such irregularities may be an outcome of power source instability, noise-figure changes, and changes in the attenuation of the electromagnetic waves which are caused by fluctuations in the gap between the antenna and the skin. Using multi antenna elements and/or multi transducers allows identifying and/or reducing and/or factoring out noises and disturbances. By separately tracking reflections from different sub areas of the monitored tissue and/or organ, noises and disturbances may be separated, for example by detecting similar irregularities in reflections from different tissues.

In such cases array of transducers 401 may separate the reflection.

The wearable monitoring apparatus 400 may direct some or all of the transducers to capture reflection from a certain tissue or split it over separate tissues or connective tissues.

In some embodiments of the present invention, the wearable monitoring apparatus 400 implements one or more gating techniques for gating the reflected EM waves. Such gating techniques allow synchronizing the monitoring with cyclic physiological processes, such as the breathing cycle and the pace of the heart beats. The time gating techniques may be used for focusing on reflections from the pulmonary tissue. However, time gating may not separate reflections if the reflections are adjacent to one another on the time axis. Optionally, the spatial separation is improved by beaming the microwave from one transducer and capturing the reflections from another transducer. Optionally, the wearable monitoring apparatus, for example as described in FIGS. 11 and 12, beams EM waves from one of the antenna elements 401 and captures the reflections thereof from one or more other antenna elements. Optionally, the beamed EM waves are directed to form a phased-array antenna with directivity pointing with some angle to the desired reflection 405. In such a manner, the backscattering radiation is scattered in an angle which is relatively wide, for example in relation to the backscattering radiation that is beamed and captured by the same transducer. Optionally, where beams of the transmitting and intercepting transducers do not overlap, reflections resulting from tissue transitions are received off-beam and attenuated. In such a manner, the reflections from the borders of the tissue are not attenuated and the desired reflections are kept in there original intensity.

Optionally, one or more intercepting transducers are focused on the reference tissue while other intercepting transducers are focused on the desired pulmonary tissue. Optionally, two or more different intercepting transducers are focused on one or more reflection points.

As described above, the reflected EM waves may be gated during and/or before the analysis process. Using multiple transmitters, as depicted in FIGS. 11 and 12, may be used for increasing the separation between different reflections which are intercepted by the wearable monitoring apparatus. Optionally, the beams a microwave is a CW, as described in the co filed application. Optionally, the CW is a chirp in which the frequency increases or decreases with time. In such an embodiment, multiple-antenna-elements may be used to transmit and receive the CWs and still have focusing capabilities. For example, one radiating transducer may distribute its radiation across a wide area while the reception is phased by several transducers. In another example, a phased-array forms several beams which are directed to different locations. Optionally, some or more of the transducers includes phase shifters which are designed to point to the desired location. The positioning of a phase-shifter may be adjusted according to the requirements of the reference chest model. Optionally, the phase-shifter is dynamically adjusted according to the analysis of the received reflections. For example, the phase-shifter may be directed to intercept a fat-to-muscle reflection by identifying a strong pass and an opposite-signed reflection from muscle-to-lung.

Optionally, phase-shifters are used for maximizing the amplitude of the waveform of the received reflections. The waveform variance may be affected by the breathing cycle and/or by the dielectric changes of the pulmonary tissue. For example, the phase-shifters are used for maximizing the amplitude of periodic signals such as the signal that reflects the breathing process or the heart beating process.

The intensification of the waveform variance may be used for emphasizing in the small changes in the dielectric coefficients of the pulmonary tissue and for focusing the beam on the pulmonary tissue and/or on lungs transitions. Maximizing the waveform variance resulting from breathing cycles may be measured by correlating between the received reflections and separate measurements of the monitored user breathing.

In some embodiments of the present invention, the wearable monitoring apparatus 400 is adjusted according to the physical and anatomical condition and/or medical history of the monitored user. Optionally, the configuration is performed, either automatically and/or manually, after the wearable monitoring apparatus 400 is attached to user's body. Optionally, a configuration process is associated with the initial placement of the wearable monitoring apparatus 400. The automatic configuration may be based on measurements which are preformed in real time. Optionally a semi-manual configuration process is used where the user and/or the treating caretaker are required to enter medical data and/or to select a monitoring pattern and\or define various thresholds for notifications of either the medical treating team and/or the user. Optionally, the area of the receiving and/or transmitting element may be adapted to the physiology of the user. If the user has relatively thick layers of fat, larger antenna element or elements may be used in order to increase the sensitivity and the effective monitoring range. Optionally, the transducer may be defined to transmit more energy in order to improve the sensitivity of the wearable monitoring apparatus.

Reference is now made to FIG. 13, which is a flowchart of a method for monitoring the thoracic tissue fluid level of a patient using a plurality of transducers, according to some embodiments of the present invention. After the process is initiated, as shown at 800, for example in response to the activation of the wearable monitoring apparatus 400 or the aforementioned stationary or semi stationary apparatus, reflections of EM radiation emitted from the thorax are captured by the antenna elements, as shown at 801. Each antenna element performs one or more instantaneous measurements of the captured reflections. Optionally, each instantaneous measurement is defined as an average of multiple reflections. Such an average increases the signal to noise ratio (SNR) of the respective antenna element. Optionally, each antenna element captures EM radiation during one or more physiological cycles, such as respiration cycles. Optionally, the captured reflections have been emitted in a noncontinuous manner. For example, the emitting elements may be intermittently silent for a period of one or more minutes, thereby minimizing the radiation and the energy consumption. As shown at 802, the captured EM radiation and/or the signal which is generated based thereupon are filtered. The signal may be filtered by one or more of the following: sampling filters, amplifying filters, band pass filters, and matched filters.

Optionally, as shown at 808, the filtering is based on the posture of the patient during the capturing of the EM reflection, as shown at 801. In such an embodiment, reflection which has been captured with the patient is in a posture which is defined as not suitable for analysis, such as a posture that substantially changes the dielectric related property of the monitored tissue, is not analyzed. Optionally, the detection of a posture which is not suitable for reflection analysis triggers an alert, recorded for future analysis, and or added to a report, as shown at 810. The posture detection is optionally performed using the aforementioned posture detection unit.

Optionally, as shown at 809, the filtering is based on the placement of a biological activity probe, such as the probe of the wearable monitoring apparatus 400 or the aforementioned stationary or semi stationary monitoring apparatus. In such an embodiment, reflection which have been captured will the probe of the wearable monitoring apparatus 400 or the aforementioned stationary or semi stationary monitoring apparatus is misplaced or disengaged, as described in the co filed application and above. Optionally, the detection of a placement which is not suitable for capturing reflection for the analysis triggers an alert, recorded for future analysis, and or added to a report, as shown at 810. The placement detection is optionally performed using the aforementioned placement detection unit.

Now, the captured EM radiation is analyzed, as shown at 803. Optionally, the reflections from the thoracic tissues, such as pulmonary tissues, are identified, for example as described above. Optionally, as shown at 804, the identification is performed after the effect of the posture of the patient on the thoracic tissue fluid level has been identified, for example as described above and in the co filed application. Optionally, as shown at 805, the identification is performed after the received EM radiation has been modulated according to one or more physiological cycles, such as a breathing cycle, for example as described above.

Optionally, as shown at 806, data from other medical sensors is received, for example as described above. This data, when combined with the output of the analysis 803, allows classifying the clinical state of the user, optionally according to a predefined index, for example as described above. As depicted in 808, this process is repetitive and therefore allows monitoring the patient, as further described above.

The data from the analysis shown at 803, optionally in combination with the data from the external medical sensors which is shown at 806, allows classifying the pathological, clinic and/or physical state of the monitored thoracic tissue, at shown at 807. Optionally, the classification triggers an alert, report, and/or a record, for example as described in the co filed application and shown at 810.

As the wearable monitoring apparatus 400 or the aforementioned stationary or semi stationary monitoring apparatus allows the acquisition of reflections from multiple antennas, different regions may be compared to allow the elimination of motion effects. Moreover, the use of multiple antennas enables estimating the vital signs separately by each antenna. In such an embodiment, each antenna may be placed optimally to measure a specific vital sign. For example, respiration parameters could be measured by an antenna positioned anterior on the chest and congestion parameters from the mid-axillary line and heart parameters.

Medical Information

In some embodiments of the present invention, additional information about the patient may be used. Optionally, the method which is described in FIGS. 1 and 3 includes adjusting the chest wall model, the adjustment process, the breathing cycle and/or the analysis of the reflected EM radiation. Optionally, the wearable monitoring apparatus allows a user to define medical information that is related to the patient, such as pathological characteristics, age, sex, weight, height, and/or any other medical information that effect the volume and/or the functioning of the lungs. Optionally, the wearable monitoring apparatus allows setting a baseline that reflects a certain clinical level and associating the measured values therewith. Defining such a baseline may increase the diagnostic sensitivity of the wearable monitoring apparatus to changes on the thoracic tissue fluid level. For example, congestive heart failure (CHF) patients are admitted predominantly with lungs with 90% or more lung fluid content compared to a normal lung. The monitoring of the drying-up treatment given at the medical center, can be used for adjusting the range of pathological to stabilized parameter values. Thus, allowing tuning up the parameters and the thresholds.

Additional parameters from external devices may be integrated into the system to provide higher monitoring capabilities and to increase the diagnosis capabilities. Parameters such as oxygen saturation and blood pressure may be acquired by dedicated devices in response to a demand by the system or according to periodical presets. These parameters are considered by the machine learning algorithms to enhance the diagnosis capability and to reduce false alarms. Optionally, a medical treating team may be provided with a more comprehensive picture of the patient status and of the processes the patient goes through. These additional parameters may be used in a similar manner to the parameters extracted directly from the analyzed reflection of EM radiation, for example for adjusting the signals, analyzing proper attachment of the device, posture registration, and the like.

Additional sensors such as accelerometers and tiltmeters may provide additional information in a manner that allows classifying the current posture and\or activation of the patient, thus increasing the accuracy of the system to detect such events and therefore improve the monitoring and/or diagnosis capabilities.

It is expected that during the life of a patent maturing from this application many relevant methods and systems will be developed and the scope of the term a microwave, a transmitter, a receiver, and/or a device are intended to include all such new technologies a priori.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as patient numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as patient numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each patient publication, patent or patent application was specifically and patiently indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for determining a pulmonary fluid content level in at least one thoracic tissue using at least one hardware processor and at least one antenna element, comprising:
   radiating and intercepting, using at least one antenna element, radio frequency (RF) radiation at a range of 0.3 gigahertz (GHZ) to 20 GHZ to and from the at least one thoracic tissue of a patient in each of a plurality of radiation sessions;
   identifying a differential signal from a difference between RF signals extracted from said RF radiation during one of said plurality of radiation sessions;
   using at least one hardware processor to extract at least one feature from the differential signal, said at least one feature is selected from a group consisting a phase and an amplitude of the differential signal;
   detecting a dielectric related property of the at least one thoracic tissue according to said at least one feature;
   determining a pulmonary fluid content level in said at least one thoracic tissue according to said dielectric related property; and
   outputting a notification based on said pulmonary fluid content level.

2. The method of claim 1, wherein at least some of said intercepting is performed when said patient is ambulatory.

3. The method of claim 1, wherein said dielectric related property is detected by identifying a segment representing said at least one thoracic tissue, and detecting said dielectric related property according to said segment.

4. The method of claim 3, wherein said dielectric related property is detected by using a predefined chest wall model for identifying said segment.

5. The method of claim 4, further comprising adjusting said predefined chest wall model according to at least one of medical information, a predefined cycle, and imaging data related to said patient.

6. The method of claim 1, wherein said determining comprises identifying a breathing cycle of said patient.

7. The method of claim 1, further comprising identifying a posture of said patient; wherein said determining is performed with respect to the effect of said posture on said dielectric related property.

8. The method of claim 1, further comprising identifying an activity level, said determining being performed with respect to the effect of said activity level on a dielectric related property of the at least one thoracic tissue.

9. The method of claim 1, further comprising identifying a pattern of a change in said pulmonary fluid content, said pattern of a change being indicative of at least one of a pathologic pattern, wherein said notification is configured for indicating said at least one pathologic pattern.

10. The method of claim 9, wherein said at least one pathologic pattern is of a member selected from a group consisting of: a degenerative process, acute respiratory distress syndrome (ARDS), congestive heart failure (CHF), trauma, an atelectasis, a post-operative atelectasis, a post-operative process, an osculated bronchus, a pulmonary inflammation progress, a pulmonary blood accumulation, an infectious causes, an inhaled toxins, a circulating exogenous toxins, a vasoactive substances, a disseminated intravascular coagulopathy (DIC), a immunologic processes reactions, a uremia, a post drowning lung water level, a pulmonary venous thrombosis, a stenosis, a veno-occlusive disease, a hypoalbuminemia, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, and post-cardiopulmonary bypass.

11. The method of claim 1, further comprising monitoring a biological parameter of said patient using a medical sensor, said determining being performed according to a combination of data based on said RF radiation and said biological parameter.

12. The method of claim 11, wherein said medical sensor is selected from a group consisting of an electrocardiogram (ECG), an electromyogram (EMG), an ultrasound transducer, a pulse oximeter, a blood pressure sensor, coagulometer, and optical blood saturation detector.

13. The method of claim 1, wherein further comprising identifying a current position of said at least one antenna element with respect to said at least one thoracic tissue; wherein determining is performed with respect to the effect of said current position on said dielectric related property.

14. The method of claim 1, wherein said dielectric related property is indicative of at least one tissue transition.

15. The method of claim 1, further comprising identifying a breathing cycle of said patient and modulating said RF radiation according to said breathing cycle.

16. The method of claim 1, wherein said determining comprises identifying a buildup of thoracic tissue fluid level in a pathological pace according to an analysis of said dielectric related property; wherein said notification is indicative of said buildup.

17. The method of claim 1, wherein said buildup reflects a trend of said thoracic tissue fluid level during said period of at least 24 hours.

18. The method of claim 1, wherein said difference is induced by a cyclic physiological process selected from a group consisting of a breathing cycle and a pace of heart beats.

19. A monitoring apparatus configured to determine a pulmonary fluid content level in at least one thoracic tissue using at least one hardware processor and at least one antenna element, said monitoring apparatus comprises:
  a probe having at least one antenna element to radiate and intercept at least one radio frequency (RF) radiation at a range of 0.3 gigahertz (GHZ) to 20 GHZ to and from at least one thoracic tissue of a patient;
  at least one hardware processor adapted to:
  identify a differential signal from a difference between signals extracted from said RF radiation,
  extract at least one feature from the differential signal, said at least one feature is are selected from a group consisting a phase and an amplitude extracted from said differential signal,
  detect a dielectric related property of at least one thoracic tissue according to said at least one feature, and
  determine a pulmonary fluid content level in said at least one thoracic tissue according to said dielectric related property;
  wherein said probe and said at least one hardware processor are configured for respectively performing said interception and said RF signal analysis in a plurality of radiation sessions.

20. The monitoring apparatus of claim 19, further comprising an attachment element configured for attaching the monitoring apparatus to a thorax of said patient.

21. The monitoring apparatus of claim 19, wherein said monitoring apparatus is substantially stationary, said plurality of radiation sessions being performed while said patient is in a monitoring position.

22. The monitoring apparatus of claim 19, wherein said at least one hardware processor is adapted to detect said dielectric related property based on a member of a group consisting of: an accumulation of pulmonary fluid content, a dispersion of pulmonary fluid content, a concentration change in distribution of said pulmonary fluid, and a change composition of pulmonary fluid content.

23. The monitoring apparatus of claim 19, further comprising a dosage interface configured for providing treatment instructions according to said pulmonary fluid content level.

24. The monitoring apparatus of claim 19, further comprising an interface configured for communicating with a medical device adapted to examine breathing volumes of said patient, said at least one hardware processor being configured for performing said determining according to said breathing volumes.

25. The monitoring apparatus of claim 19, wherein said at least one hardware processor is configured to determine a pathological indicator according to said pulmonary fluid content level; further comprising an output unit for generating a notification in response to said pathological indicator.

26. The monitoring apparatus of claim 19, further comprising an adjustment unit for receiving adjustment information related to said patient, said at least one hardware processor configured for performing said determining according to said adjustment information.

27. The monitoring apparatus of claim 19, wherein said probe having a plurality of antenna elements for transmitting and intercepting the RF radiation from a plurality of different areas.

28. The monitoring apparatus of claim 19, wherein said at least one hardware processor reduces an effect of a member of a group consisting of: a posture change, a change in placement, and a change in a power of said RF radiation.

29. The monitoring apparatus of claim 19 wherein said at least one hardware processor is adapted for executing a code for generating a notification to a user according to said pulmonary fluid content level in light of at least one user defined threshold.

30. The monitoring apparatus of claim 19, wherein said at least one hardware processor is adapted for executing a code for performing at least one of:
  monitoring the placement of the monitoring apparatus on the body of said patient in relation to an internal tissue, and
  identifying at least one of misplacement, displacement, and disengagement of said monitoring apparatus in relation to an internal tissue.

31. The monitoring apparatus of claim 19, wherein said at least one hardware processor is adapted for executing a code for controlling a mechanical adjustment to change a position of the monitoring apparatus.

32. The monitoring apparatus of claim 19, wherein said plurality of radiation sessions are intermittent.

33. The monitoring apparatus of claim 19, wherein said at least one hardware processor is configured for detecting at least one of vital signs, trends of vital signs and physiological process of said patient, said at least one hardware processor being configured for calculating clinical state of said patient with respect to said dielectric related property in pulmonary fluid content and to at least one said vital signs, trends of vital signs and physiological process;
  wherein said probe intercepts said at least one radio frequency (RF) radiation while the at least one thoracic tissue moves.

34. The monitoring apparatus of claim 19, wherein said determining comprises analyzing said difference in said signals among at least one of different segments of the signal and signals measured at different time instances.

35. The monitoring apparatus of claim 19, wherein during a period of said plurality of radiation sessions, said at least one hardware processor is adapted to at least one of the following:
  reduce of at least one movement effect; and
    generate guidance instructions for at least one of repositioning the monitoring apparatus and guiding the monitored patient to a posture.

36. The monitoring apparatus of claim 19, wherein during a period of said plurality of radiation sessions, said at least one hardware processor is adapted to, at least one of the following:
  detect at least one of misplacement and disengagement of the monitoring apparatus;
  identify a period for performing a data acquisition session;

identify said dielectric related property by at least one of calculating a baseline and identifying a normal range which are adjusted according to the patient; and use a tracking algorithm for compensating for relative movements of an antenna of said probe in respect to points of interest.

37. The monitoring apparatus of claim 19, wherein said at least one hardware processor reduces the effect of a movement on said dielectric related property identification, said movement comprises a member of a group consisting of: a thoracic movement, an internal physiological activity, and an external physiological activity irregularity.

38. The monitoring apparatus of claim 19, wherein said at least one hardware processor reduces the effect of a movement on said dielectric related property identification, said movement is a member of a group consisting of: an organ movement, an antenna movement, a change of posture movement, a bodily movement, an activity related movement.

39. A method for determining a pulmonary fluid content level in at least one thoracic tissue using at least one hardware processor and at least one antenna element, comprising:

intercepting, using at least one antenna element, at least one radio frequency (RF) the range of 0.3 gigahertz (GHZ) to 20 GHZ from the at least one thoracic tissue of a patient in a plurality of radiation sessions;

using at least one hardware processor for:

identifying a differential signal from a difference between signals extracted from said RF radiation;

extracting at least one feature from the differential signal, said at least one feature is selected from a group consisting of: a phase and an amplitude of said the differential signal;

detecting a dielectric related property of the at least one thoracic tissue according to said at least one feature;

determining a pulmonary fluid content level in said at least one thoracic tissue according to said dielectric related property; and outputting a notification indicating said pulmonary fluid content level.

* * * * *